US005756678A

United States Patent [19]
Shenoy et al.

[11] Patent Number: 5,756,678
[45] Date of Patent: May 26, 1998

[54] PRION INACTIVATION IN CONNECTIVE TISSUE MATERIALS

[75] Inventors: Vivek N. Shenoy, Sunnyvale; Timothy T. Revak, Los Altos, both of Calif.

[73] Assignee: Cohesion Technologies, Inc., Palo Alto, Calif.

[21] Appl. No.: 431,950

[22] Filed: May 1, 1995

[51] Int. Cl.⁶ .............................. A61K 38/17; C12N 7/06
[52] U.S. Cl. ...................... 530/356; 530/402; 530/410; 514/8; 514/21; 514/801; 435/236; 435/238
[58] Field of Search ........................... 530/356, 402, 530/410; 514/8, 21, 801; 435/236, 238

[56] References Cited

U.S. PATENT DOCUMENTS

| | | | |
|---|---|---|---|
| 3,131,130 | 4/1964 | Oneson | 195/6 |
| 3,530,037 | 9/1970 | Nishihara | 195/6 |
| 4,511,653 | 4/1985 | Play et al. | 435/69 |
| 5,616,689 | 4/1997 | Shenoy et al. | 530/356 |

FOREIGN PATENT DOCUMENTS

| | | |
|---|---|---|
| 2140834 | 7/1995 | Canada. |
| 0667352 | 8/1995 | European Pat. Off. . |

OTHER PUBLICATIONS

Steinbach, *Arzneim–Forsch/Drug Res.*, No. 42 (I), Nr. 1, pp. 85–89, 1992.
Brown et al. *The J. of Infectious Diseases*, vol. 153, No. 6, pp. 1145–1148, 1986.
Taylor et al, *Arch. Virol.*, vol. 139, pp. 313–326, 1994.
P. Brown et al., "Newer Data on the Inactivation of Scrapie Virus or Creutzfedt–Jakob Disease Virus in Brain Tissue", *The J. of Infectious Diseases*, vol. 153, No. 6, pp. 1145–1148 (1986).
Wallace et al., "Multiple Denaturational Transitions in Fibrillar Collagen", *Biopolymers*, vol. 25, pp. 1875–1893 (1986).
Dr. Steinbach, "Recommendations for Minimizing the Risk of Infection by Agents Causing Zoonoses and Other Animal Infections in Manufacture of Medicinal Products", *Arzneim–Forsch/Drug Res.*, No. 42 (I), Nr. 1, pp. 85–89 (1992).

"Public Health Issues Related to Animal and Human Spongiform Encephalopathies: Memorandum from A WHO Meeting", *Bulletin of the World Health Organization*, No. 70 (2), pp. 183–190 (1992).

D.R. Ernest et al., "Comparative Analysis of Scrapie Agent Inactivation Methods", *J. Vicological Methods*, 41:193–202 (1993).

S.B. Prusiner, "Biology and Genetics of Prion Diseases", *Annu. Rev. Microbiol.*, 48:655–686 (1994).

D. M. Taylor et al., "Decontamination Studies with the Agents of Bovine Spongiform Encephalopathy and Scrapie", *Arch. Virol.*, 139:313–326 (1994).

*Primary Examiner*—Cecilia J. Tsang
*Assistant Examiner*—Abdel A. Mohamed
*Attorney, Agent, or Firm*—Morrison & Foerster

[57] ABSTRACT

It has been discovered that it is possible to treat solutions of connective tissue material for the inactivation of prions in a manner such that connective tissue molecules are not adversely affected by the inactivation treatment. For example, solubilized atelopeptide collagen can be treated with sodium hydroxide for the inactivation of prions and other infectious agents without affecting the ability of the solubilized collagen to form stable fibers. In accordance with the present invention, a first method for the treatment of connective tissue materials such as collagen for the inactivation of prions and other infective agents, to obtain at least 5 logs of protection, comprises the following steps:

a) placing the connective tissue material into a liquid solution, whereby the surface area of the connective tissue molecules is exposed, to expose the prions and other infectious agents for treatment; and b) contacting the liquid solution of connective tissue material with sodium hydroxide so that the concentration of sodium hydroxide in said solution ranges from about 0.1M to about 0.7M, for a time period sufficient to inactivate the prions and other infective agents without affecting the performance of the connective tissue material, at a temperature of about 25° C. or less.

18 Claims, 11 Drawing Sheets

# 5,756,678

PRION INACTIVATION IN CONNECTIVE TISSUE MATERIALS

BACKGROUND OF THE INVENTION

1. Field of the Invention

The present invention relates to a method of treating connective tissue molecules for the deactivation of infectious agents, and particularly prions.

2. Description of the Background Art

Stanley B. Prusiner of the Department of Neurology and Biochemistry and Biophysics, University of California, San Francisco has recently authored a number of papers describing the "remarkable discoveries in the past three decades (which have) led to the molecular and genetic characterization of the transmissible pathogen causing scrapie in animals and a quartet of illnesses in humans: Kuru, Creutzfeldt-Jacob Disease (CJD), Gerstmann-Straussler-Scheinker disease, and Fatal Familial Insomnia. To distinguish this infectious pathogen from viruses and viroids, the term PRION was introduced to emphasize its proteinaceous and infectious nature." There are various hypotheses for the structure of the infectious prion particle, and these include: 1) proteins surrounding a nucleic acid that encodes them; 2) proteins which are associated with a small polynucleotide; and 3) proteins which are devoid of nucleic acid. Dr. Prusiner argues for hypothesis 3); in any case, the unique features of prion structure and propagation differentiate prions from all other transmissible pathogens.

In "Biology and Genetics of Prion Diseases" *Annu. Rev. Microbiol.* (1994) 48:655–686, Dr. Prusiner described the development of the prion concept and human prion diseases. He describes the accidental transmission of CJD to humans via corneal transplantation, contaminated electroencephalogram electrode implantation, and surgical operations using contaminated instruments or apparatuses (where the preparative procedures used were inadequate to inactivate human prions). Thus, prions are transmissible pathogens which require their own unique inactivation processing to ensure protection of the general public from infection.

In addition, there are public health issues pertaining to the use of animal and human tissues in medical devices which are implanted into human beings, to the use of such tissues in pharmaceuticals, and to a lesser degree, to use in cosmetics. Of particular concern is the potential presence of prions in such tissues, which prions are particularly difficult to deactivate.

U.S. Pat. No. 4,511,653 to Play et al., issued Apr. 16, 1985, describes a process for the industrial preparation of human collagenous material from human placental tissue. This process includes subjecting the placental tissue to an alkaline treatment with a 0.5M solution of sodium hydroxide (NaOH), a 0.5M solution of potassium hydroxide (KOH), or a saturated lime water solution at a temperature of less than or equal to 10° C., for purposes of inactivation of hepatitis viruses. The placental collagen which is treated with sodium hydroxide is insoluble collagen, wherein approximately 10% to 20% of the collagen treated is solubilized by the sodium hydroxide treatment. This process is said to offer the advantage of providing for hepatitis deactivation while facilitating the subsequent solubilization of up to 20to 35% of the total collagen without the use of proteolytic enzymes.

In June of 1986, *Concise Communications*, the Journal of Infectious Diseases, Vol. 153, No. 6, there is a description of the inactivation of prions, such as scrapie and CJD present in 20% brain homogenates, using various concentrations of sodium hydroxide for one hour at room temperature.

In September of 1991, Recommendations for Minimizing the Risk of Infection by Agents Causing Zoonoses and Other Animal Infections in the Manufacture of Medicinal Products, *Federal Journal of Official Publications* (BAnz., Germany), No. 164, p.6120, there is the description of the treatment of medical materials with a solution of 1N (1M) NaOH for one hour at 20° C. for the purpose of inactivation of infectious agents. This treatment was recommended particularly for application to bovine spongiform encephalopathy (BSE) and materials of bovine origin.

In 1992, Public Health Issues Related to Animal and Human Spongiform Encephalopathies: Memorandum from a WHO Meeting, *Bulletin of the World Health Organization*, 70(2): pp 183–190, a discussion is presented regarding BSE, a member of the group of transmissible spongiform encephalopathies (TSE) whose prototype is scrapie. Treatment of medicinal products derived from bovine tissues with NaOH, preferably 1M, for 1 hour at 20° C. is recommended as a manufacturing process for removal or reduction of BSE infectivity.

Darwin R. Ernst and Richard E. Race, in "Comparative analysis of scrapie agent inactivation methods", *Journal of Virological Methods*, 41 (1993) 193–202, describe inactivation treatments for scrapie-infected hamster brain homogenate. Inactivation treatments utilizing autoclaving for various lengths of time either alone or in combination with different concentrations of sodium hydroxide or LpH, an aqueous acid phenolic derivative, are disclosed. Although this paper indicates that treatment of suspensions of hamster brain using either 0.1N or 1.0N NaOH alone was carried out, no data are presented.

D. M. Taylor et al., in "Decontamination studies with the agents of bovine spongioform encephalopathy and scrapie", *Arch. Virol.* (1994) 139 :313–326, describe the use of sodium hydroxide to treat macerates of bovine brain infected with bovine spongiform encephalopathy (BSE) agent; rodent brain infected with the 263K strain of scrapie agent; and, rodent brain infected with the ME7 strain of scrapie agent. The macerates were exposed for up to 120 minutes to 1.0M or 2.0M sodium hydroxide, but "no procedure produced complete inactivation of all agents tested". Taylor et al. explained that their study was carried out due to inconsistencies in the data from various laboratories. They found that the data from the NaOH inactivation experiments demonstrated that none of the combinations of time (30 min up to 120 min) and molarity (1M and 2M) produced consistent inactivation of BSE and scrapie agents. Further, there was the unexplained finding in the NaOH experiments that with the 263K strain, with BSE, and possibly with ME7, two hours of exposure were less effective than exposure periods for 30 or 60 minutes.

Collagen Corporation, assignee of the present application, produces a variety of products having bovine collagen as a principal component. Further, Collagen is developing products which include a number of connective tissue materials useful in the repair and replacement of damaged human or animal connective tissues. Examples of such connective tissue materials include collagen, fibrin (and its precursor fibrinogen), mucopolysaccharides, fibronectin, elastin, and proteoglycans, by way of illustration and not by way of limitation. Although collagen is distinctive in forming insoluble fibers among the connective tissue materials, these materials have a number of features in common, including the characteristic that they are large, bulky molecules which tend to bind to other connective tissue molecules or to themselves via crosslinking reactions. As a result of the tendency of these molecules to bind together to form fibrous chains which become crosslinked or entangled into matrices, prion deactivation can be difficult, since it is necessary for the deactivating agent to reach the prion (which may be surrounded by a protective matrix of connective tissue material).

Donald G. Wallace et al. in "Multiple Denaturational Transitions in Fibrillar Collagen", *Biopolymers*, Vol. 25, 1875–1893 (1986), describes heat denaturation of pepsinized bovine fibrillar collagen, wherein differential scanning calorimetry (DSC) was used to study heat denaturing transitions of the collagen fiber. It was proposed that collagen fibers reconstituted from solutions of collagen are comprised of several distinct fibrillar species, which may correspond to multiple melting endotherms observed during the DSC heat denaturing of the collagen fiber.

Pending patent application Ser. No. 08/274,673 of Shenoy et al., assigned to Collagen Corporation as well, and which is hereby incorporated by reference in its entirety, describes the treatment of solutions or dispersions of collagen with a chemical reagent for the inactivation of infectious agents. In particular, such dispersions and solutions were treated using a 1M concentration of sodium hydroxide for a period of approximately one hour at about 20° C. The collagen fibers subsequently produced from the treated solutions or dispersions differed substantially from collagen fibers produced from solutions or dispersions which had not been treated with NaOH. The difference in collagen fibers was indicated by DSC data, opacity data for suspensions of the collagen fibers, and physical properties of the fibers in various formulations. The sodium hydroxide treatment of collagen molecules in solution had destabilized the collagen fibers which were subsequently precipitated from the solution. To stabilize the collagen fibers, Shenoy et al. used a physical fiber-stabilizing agent. The physical fiber-stabilizing agent protects the stability of the fibers (weakened by the sodium hydroxide treatment) as they are formulated into various products which expose the fibers to solvents, or agents which cause fiber dissociation into subassemblies, such as lidocaine or high salt concentrations. In an alternative, preferred, method of stabilizing the fibers, a chemical reagent (preferably a crosslinker) is used, subsequent to the sodium hydroxide treatment to stabilize the collagen fiber after its formation. Although collagen fibers prepared using these stabilization techniques can meet the product specifications for numerous products (previously made without sodium hydroxide treatment for prion inactivation), there may be applications where the stabilized fibers are not able to meet the product requirements.

Thus, it would be highly desirable to have a method for inactivating prions which may be present in connective tissue materials without damaging the structure of the connective tissue molecule. In particular, there is a need for a method of inactivating prions without affecting the fiber-forming capability of collagen-based connective tissue.

SUMMARY OF THE INVENTION

It has been discovered that it is possible to treat solutions of connective tissue material for the inactivation of prions in a manner such that connective tissue molecules are not adversely affected by the inactivation treatment. For example, solubilized atelopeptide collagen can be treated with sodium hydroxide for the inactivation of prions and other infectious agents without affecting the ability of the solubilized collagen to form stable fibers. Further, the fibers formed from the treated collagen exhibit the same behavior in terms of melting temperature, opacity upon examination by spectrophotometric techniques, stability in the presence of agents which tend to cause fiber dissociation into fiber subassemblies, and rate of fiber formation when compared with collagen which has not been treated with sodium hydroxide. Collagen containing the telopeptide portion of the molecule can be treated in like manner to the atelopeptide collagen. However, since, in its native form, a large portion of the collagen tends to be crosslinked in the telopeptide region, it may be necessary to remove this region of the molecule to render it soluble.

In accordance with the present invention, a first method for the treatment of connective tissue materials such as collagen for the inactivation of prions and other infective agents, to obtain at least 5 logs of protection, comprises the following steps:

a) placing the connective tissue material into a liquid solution, whereby the surface area of the connective tissue molecules is exposed, to expose the prions and other infectious agents for treatment; and b) contacting the liquid solution of connective tissue material with sodium hydroxide so that the concentration of sodium hydroxide in said solution ranges from about 0.1 Molar to about 0.7 Molar, for a time period sufficient to inactivate the prions and other infective agents without affecting the performance properties of the connective tissue, at a temperature of about 25° C. or less.

The most preferred connective tissue material of the present invention is collagen and the performance property monitored is the stability of the collagen fibers produced from the sodium hydroxide-treated solution of collagen.

Because it would be preferable to use the most dilute concentration of sodium hydroxide which provides the desired 5 logs of protection for the inactivation of prions, various concentrations of sodium hydroxide of less than 0.7M were investigated. The lower concentrations of sodium hydroxide were investigated both for effectivity in prion inactivation and effect upon the connective tissue molecule. In the case of collagen, the effect of sodium hydroxide treatment on the collagen is particularly evidenced in the stability of collagen fibers formed from the treated collagen molecules in solution. Thus, fiber stability was used as the indicator of the effect upon the collagen molecule of exposure of the molecule to the particular sodium hydroxide concentration.

Further in accordance with the present invention, it has been determined that, in a process for the treatment of collagen for the inactivation of prions and other infective agents to provide at least 5 logs of protection, without affecting the collagen molecule, at temperatures of 25° C. and less, the following time periods can be used at the sodium hydroxide concentrations specified. For a sodium hydroxide concentration of 0.5 Molar, a time period of 80 minutes or less can be used for treatment of the collagen solution to inactivate prions. For a sodium hydroxide concentration of 0.35 Molar, a time period of 90 minutes or less can be used. For a sodium hydroxide concentration of 0.25 Molar, the corresponding time period is 100 minutes or less. For a sodium hydroxide concentration of 0.10 Molar, the corresponding time period is 150 minutes or less.

DETAILED DESCRIPTION OF THE INVENTION

Figure 1:
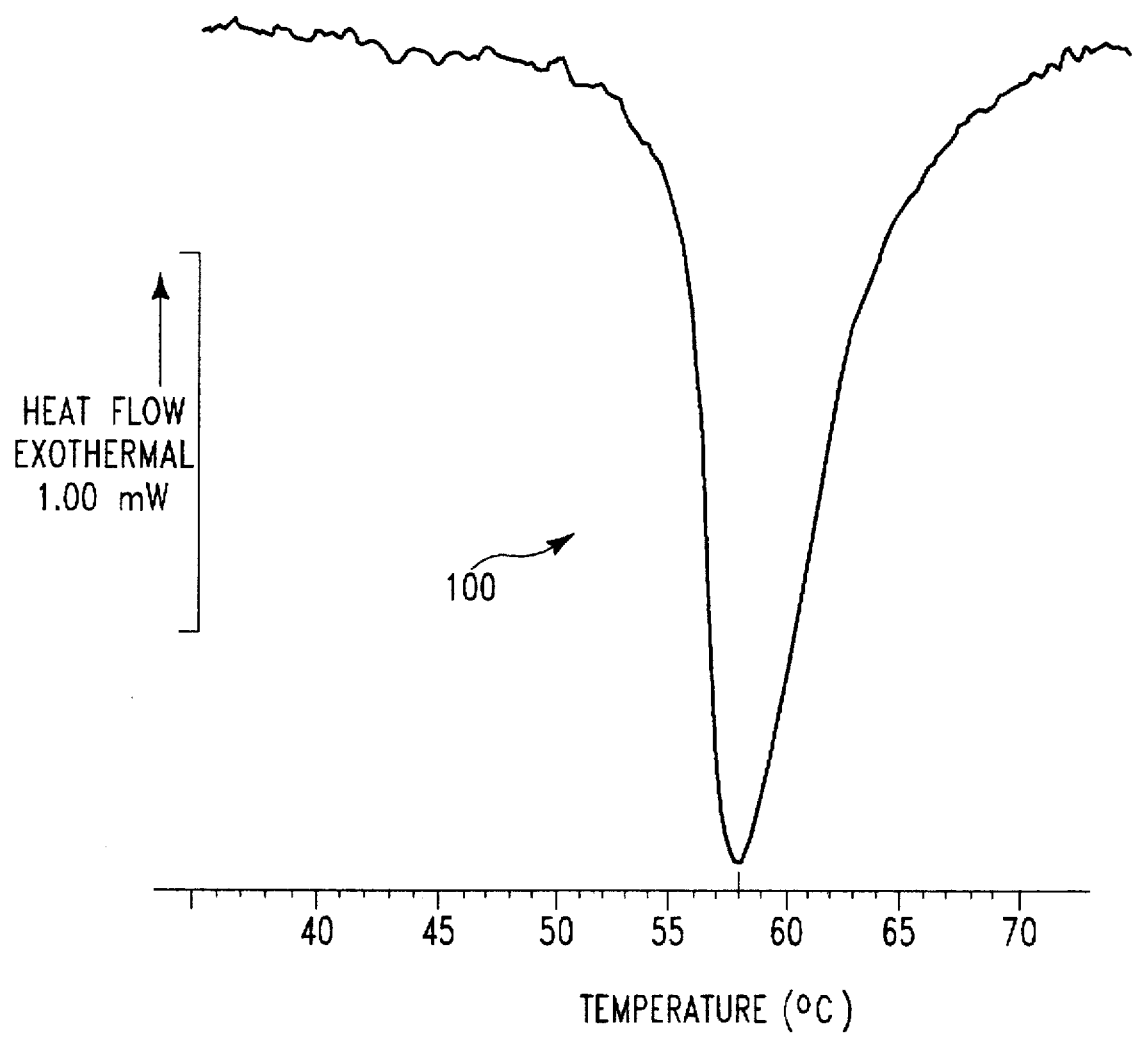
FIG. 1 illustrates the differential scanning calorimetry (DSC) curve for atelopeptide collagen fibers which were produced from collagen in solution where the length of time the collagen molecules in solution were exposed to sodium hydroxide was carefully controlled. The maximum sodium hydroxide concentration during treatment of the collagen molecules in solution was 1M; the treatment temperature was about 20° C.; and the time period at the 1.0M concentration was about 60 minutes. The concentration of sodium hydroxide was then immediately reduced to about 0.11M by the addition of a large volume of 4° C. water, followed by neutralization with hydrochloric acid. Collagen fibers were subsequently precipitated from solution and formulated to 35 mg/ml of protein without the presence of a salt or lidocaine.

As a preface to the detailed description, it should be noted that, as used in this specification and the appended claims, the singular forms "a", "an", and "the" include plural referents, unless the context clearly dictates otherwise. Thus, for example, the term "a collagen fiber" includes one or more fibers, reference to a "subassembly fiber group" includes all of the various components of that subassembly unit, and reference to "the collagen" includes mixtures of different types of collagens and so forth.

Specific terminology of particular importance to the description of the present invention is defined below:

The term "atelopeptide collagen" refers to collagens which have been chemically treated or otherwise processed to remove the telopeptide regions, which are known to be responsible for causing an immune response in humans to collagens from other animal, such a bovine, sources.

The term "collagen" as used herein refers to all types and forms of collagen, including those which have been extracted from naturally occurring sources, such as bovine corium or human placenta, and which may have been processed or otherwise modified.

The term "collagen suspension" refers to a suspension of noncrosslinked or crosslinked collagen fibers in an aqueous carrier, such as water or phosphate-buffered solution (PBS), with or without salt.

The term "fibrillar collagen" refers to collagens in which the triple helical molecules of collagen aggregate to form fibers due to intermolecular charge and hydrophobic interactions.

The term "fiber assembly" or "assembled fiber" refers to a complete, aggregated fiber which may contain a number of fiber subassemblies.

The term "fiber subassembly" refers to an individual, distinct fibril class which is aggregated into a fiber. There are a number of distinct fibrillar classes which may represent three or more types of banded and nonbanded species that differ from each other in packing order, fibril width, and level of crosslinking.

The term "soluble collagen" or "collagen in solution" refers to collagen molecules which are solvated by surrounding media to the extent that fiber aggregates are not present or are present only in minor quantities in the form of precursor fibrils. Dissociation of fiber aggregates into collagen molecules and/or precursor fibrils results in a viscous optically clear solution.

1. The Concept

Collagen is only one of a number of connective tissue materials which are comprised of large molecules which form matrix-like structures, and although the concept of the present invention is applicable to such connective tissue materials in general, the descriptions included herein are with reference to collagen fibers.

Based on the earlier work by applicants, described in copending patent application Ser. No. 08/274,673, filed Jul. 13, 1994, now U.S. Pat. No. 5,616,689, it was known to applicants that the stability of a collagen fiber produced from collagen molecules treated in solution with 1.0M sodium hydroxide (at about 20° C. for about 60–70 minutes) was affected by the sodium hydroxide treatment. This work indicated that the sodium hydroxide treatment affects collagen molecules in a manner such that fibers formed from such molecules are not stable. The '273 application pertains to methods of stabilizing the collagen fibers which have been treated with sodium hydroxide.

The presently disclosed invention includes data showing that the collagen fiber instability is attributable to the dissociation of smaller fiber subassemblies within the main fiber assembly. The degree of fiber instability caused by the treatment depends on sodium hydroxide concentration in the solution at time of treatment; the temperature at which the treatment is carried out; and the length of time of treatment. As the concentration, temperature and time of treatment are increased, the collagen molecules are affected in a manner which increases the instability of the aggregate of subassembly fibers within the main fiber assembly. This fiber instability becomes apparent upon exposure of the fibers in suspension to a destabilizing environment such as high salt concentrations or exposure to particular active agents which cause dissociation, such as lidocaine. Presence of a larger quantity of dissociated subassembly units manifests itself in a differential scanning calorimetry curve showing an increase in the portion of the collagen fiber which melts at a lower temperature. In addition, presence of a larger quantity of disassembled subassembly units results in a lower opacity reading (indicating smaller fiber size) when suspensions of the collagen fiber are evaluated via spectrophotometric techniques.

EXAMPLE 1
1.0 Molar Sodium Hydroxide Treatment

The collagen fibers depicted in the FIG. 1 DSC curve were prepared as follows. 200 ml of soluble bovine atelopeptide collagen (3.0 mg/ml protein in an aqueous solution, pH 2.0) was brought up to 1.0M sodium hydroxide (NaOH) by the addition of 100 ml of 3.0M NaOH over a 15 minute time period. The addition of sodium hydroxide was done using a peristaltic pump and the mixture was stirred throughout the addition. The mixture was then incubated at 20° C. for 60 minutes. Immediately after the sodium hydroxide treatment period, 1600 ml (8 times the amount of soluble collagen solution) of cold water ($\approx 4°$ C.) was added to quench the sodium hydroxide treatment. The diluted mixture was neutralized with cold hydrochloric acid (HCl) ($\approx 4°$ C.) over a ten minute time period. The mixture (pH 2.0) was concentrated to approximately 3.0 mg/ml of protein and then diafiltered at constant volume against at least 4.5 volumes of 0.013M HCl.

The addition of the large volume of cold water reduced the NaOH concentration in the mixture to approximately 0.15M and the temperature to about 6° C. As a result of this quenching procedure, the effects on the collagen molecule have been attributed to the exposure to 1.0M NaOH at 20° C. for a time period of about 60 minutes. Subsequently, the collagen in solution at 3.0 mg/ml was precipitated at about 17° C. by the addition of 0.2M Disodium Phosphate buffer adjusted to a pH of 11.2 using sodium hydroxide. The volumetric ratio of collagen solution to buffer was 9:1. The precipitate produced contained a fibrous collagen concentration of approximately 2.7 mg/ml at a pH of 7.0 to 7.4. The precipitate was concentrated by centrifugation to a protein content in excess of 35 mg/ml. The centrifugate was formulated by dilution with a water-based PBS, providing a collagen suspension at 35 mg/ml in 0.02M phosphate buffer at pH 7.0 to 7.4. This final formulation was used for DSC and opacity testing.

With reference to FIG. 1, curve 100 illustrates a differential scanning calorimetry (DSC) curve for the collagen fibers which were produced in the manner described above. Because there was no salt or lidocaine present during formulation to 35 mg/ml (protein concentration in 0.02M phosphate buffer, pH 7.0 to 7.4), the effect on the collagen subassembly fibers due to treatment with sodium hydroxide is masked. Only the large assembled fiber is apparent. This large assembled fiber has a melting temperature of about 58.3° C., and an opacity of 2.1. Opacity as described herein is measured using a Beckman Spectrophotometer, Model DU 650. Collagen suspension samples at 35 mg/ml were kept refrigerated between about 4° C. and 7° C. for 24 hours prior to testing and were tested at 8° C. The spectrophotometer was blanked against water at 410 nm in a 1 mm lightpath cuvette.

EXAMPLE 2
1.0 Molar Sodium Hydroxide Treatment

Figure 2:
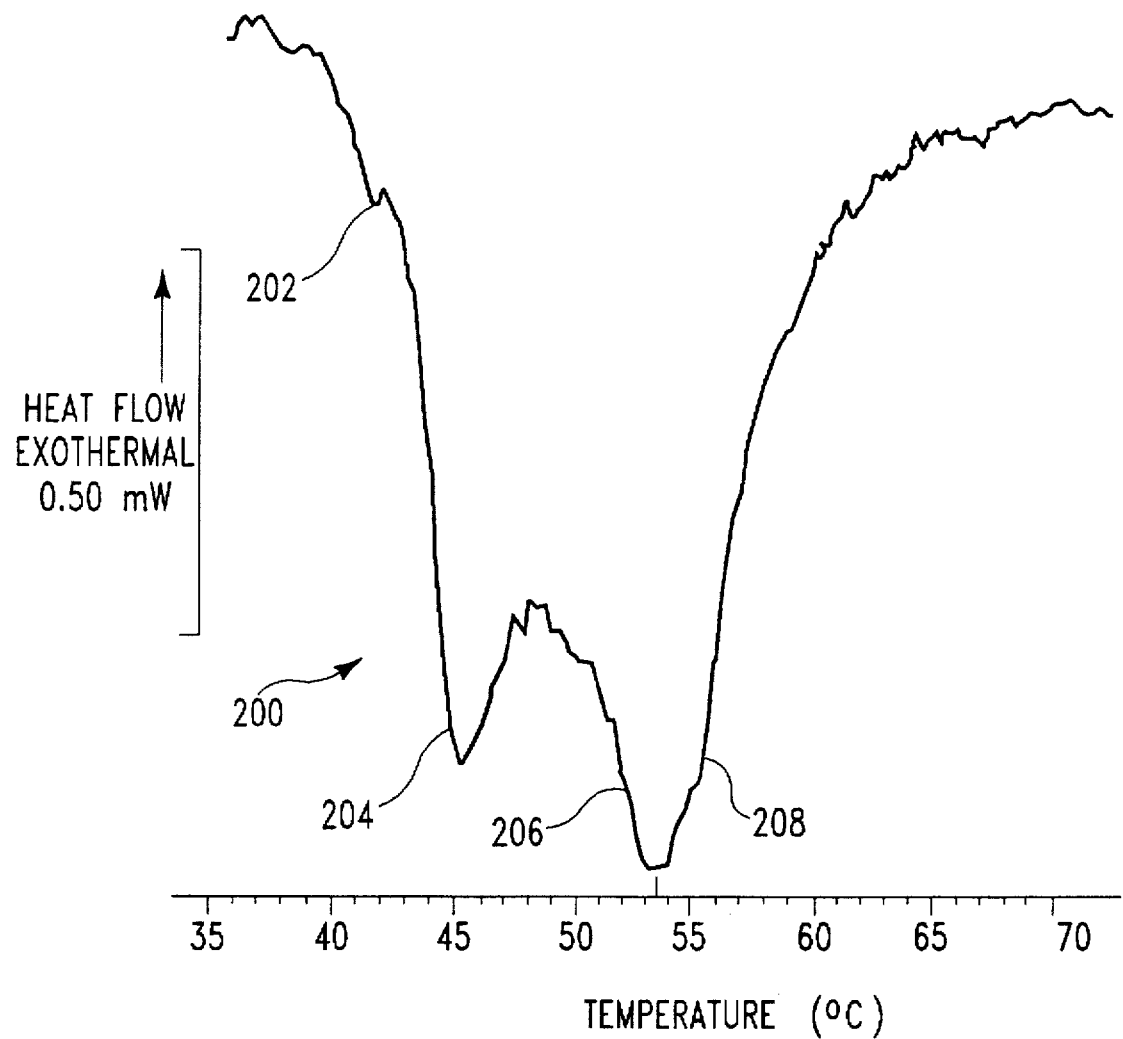
FIG. 2 illustrates the DSC curve for atelopeptide collagen fibers which were produced in the same manner as described for FIG. 1, except that 3 mg/ml of lidocaine and 0.13M NaCl were present when the fibers were formulated to 35 mg/ml of protein.

FIG. 2 shows the DSC curve 200 for the same sodium hydroxide-treated collagen molecules as those shown in FIG. 1, precipitated into fibers during the same precipitation operation. However, when the precipitated fibers were formulated to a concentration of 35 mg/ml in PBS buffer, lidocaine was present. The centrifugate was formulated by dilution with a water-based solution comprising 0.02M disodium phosphate, 3 mg/ml lidocaine (2-Diethylamino-2', 6'-acetoxylidide), and 1.3M sodium chloride, at a pH of 6.3. The resulting product comprised an aqueous dispersion containing about 35 mg/ml of fibrous collagen, 3 mg/ml of lidocaine, 0.02M disodium phosphate, and 0.13M sodium chloride, at a pH of 7.0–7.4. The lidocaine acts as an agent promoting dissociation of the large, assembled fibers into fiber subassemblies, making it clear that the stability of the large assembled collagen fiber has been affected by the sodium hydroxide treatment. The manner in which the fibers are affected is evidenced by the presence of a large amount of subassembly fibers having a lower melting point and a smaller size (as indicated by a lower opacity). For example, the DSC scan 200 includes four subassemblies. Subassembly 202, having a melting temperature of about 41.5° C., is sufficiently small that it is probably negligent in its overall effect. Subassembly 204, having a melting point of about 45° C., makes up roughly 30–45 percent of the area under the DSC curve. Subassembly 206, having a melting point of about 53.5° C., makes up roughly 50–55 percent of the area under the DSC curve. Subassembly 208, having a melting point of about 55° C., makes up a few percent of the area under the DSC curve. The opacity for the 35 mg/ml suspension of this group of subassemblies was 1.10. This reduction in opacity for the fiber assembly from 2.10 to 1.10 when lidocaine is present is further evidence of the disassembly of a large proportion of the subassembly fibers in the presence of lidocaine.

EXAMPLE 3
No Sodium Hydroxide Treatment

Figure 3:
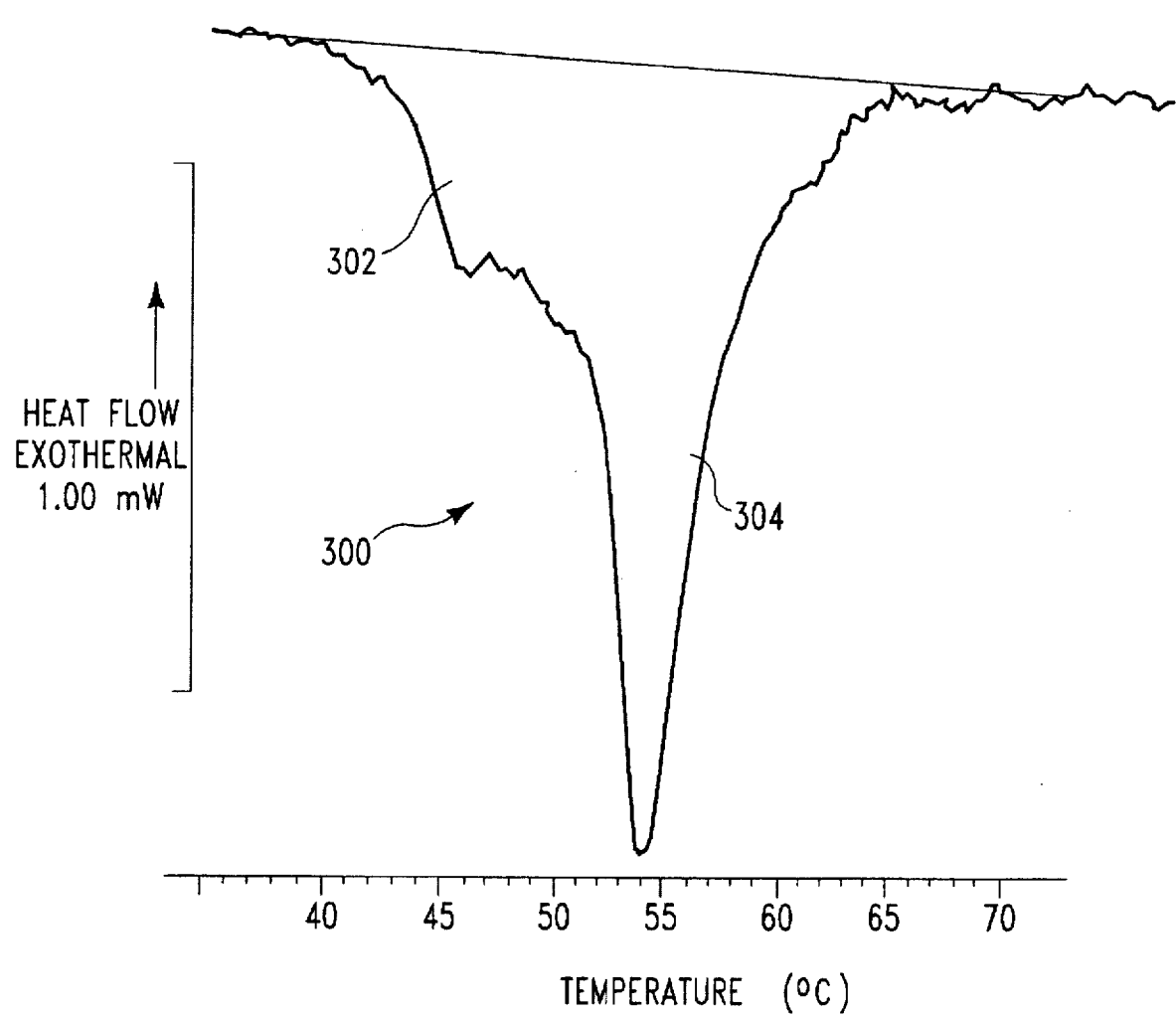
FIG. 3 illustrates the differential scanning calorimetry (DSC) curve for atelopeptide collagen fibers which were produced from collagen in solution where the collagen molecules in solution were NOT exposed to sodium hydroxide. This DSC curve represent the collagen fiber control sample. Collagen fibers precipitated from solution were formulated to 35 mg/ml of protein in the presence of 3 mg/ml of lidocaine and 0.13M NaCl.
Figure 4:
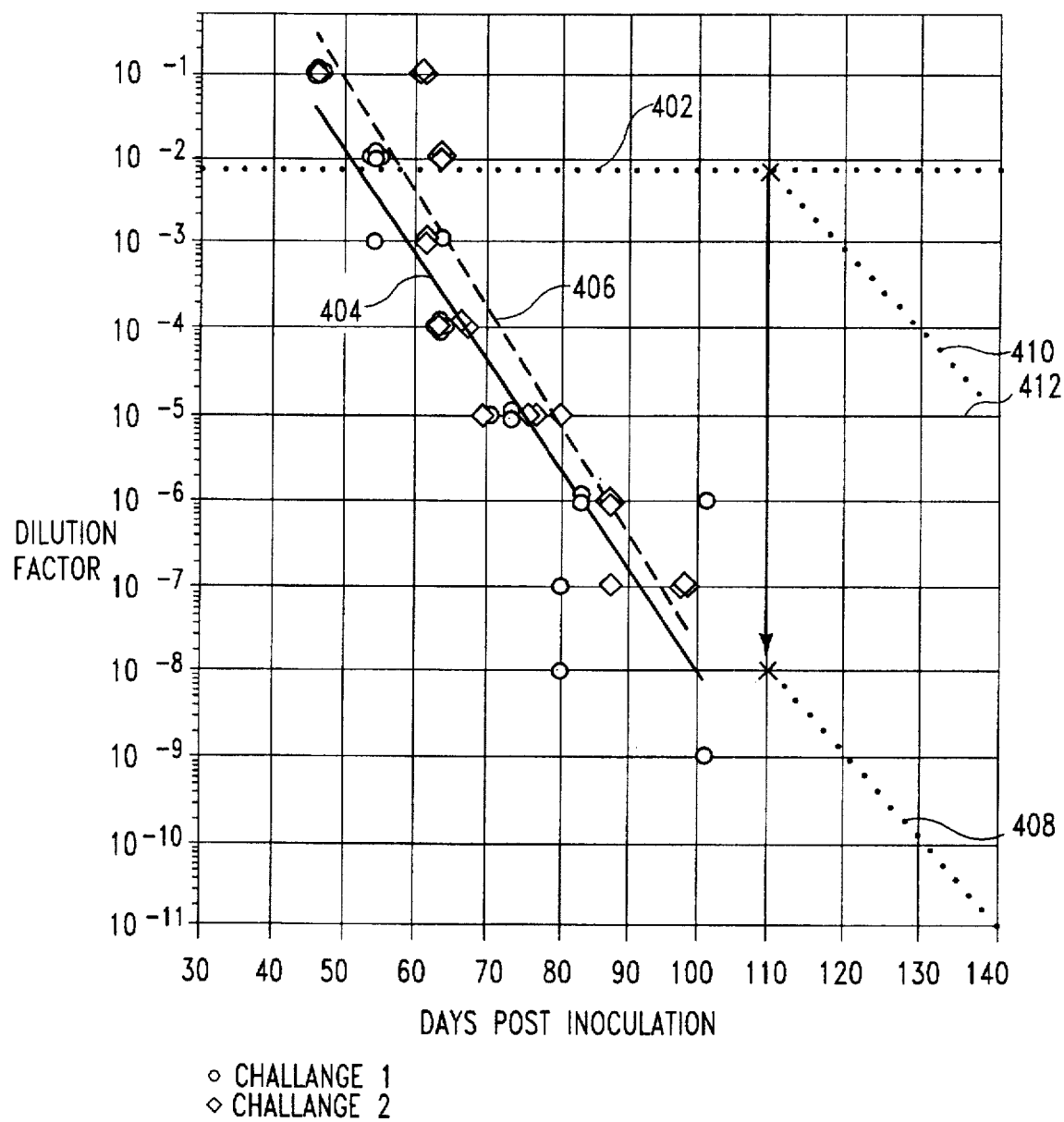
FIG. 4 shows a plot of dose response of Syrian hamsters to intercerebral inoculation with hamster brain homogenate containing hamster scrapie strain 263K. The only hamsters showing a response were those where the scrapie-containing brain homogenate was not treated with sodium hydroxide for inactivation of the prion.

FIG. 3 shows the DSC curve 300 for collagen control fibers precipitated from a solution of collagen molecules which was NOT treated with sodium hydroxide. The precipitated collagen fibers were formulated to final product at a protein concentration of 35 mg/ml in the same manner as described with reference to FIG. 2, with 3 mg/ml lidocaine and 0.13M salt present. The lidocaine again causes the large, assembled fibers to disassociate into the fiber subassemblies, showing the relative proportions of subassembly fibers which typically make up a non-sodium hydroxide-treated collagen fiber. For this control collagen fiber assembly, the DSC scan 300 includes two principal subassemblies. Subassembly 302, having a melting temperature of about 44.5° C., makes up roughly 12–15 percent of the area under the DSC scan curve. Subassembly 304, having a melting point of about 54.8° C., makes up roughly 85–88 percent of the area under the DSC curve. The opacity for the control collagen fiber-containing material shown in FIG. 3 was 1.65, compared with 1.10 for the 1.0M sodium hydroxide-treated collagen fibers, further indicating the increased quantity of disassociated smaller fiber subassembly component. Comparison of FIGS. 2 and 3 shows that the presence of lidocaine unmasks the instability of subassemblies contained in the main fiber, making the presence of lidocaine in the formulation a useful tool in determining the effect of sodium hydroxide treatment upon the collagen in solution and its ability to form stable fiber assemblies.

The degree to which subassemblies are formed which exhibit lower melting temperatures (and are of smaller fiber size) is directly related to the sodium hydroxide acting on the collagen molecule in a manner which affects fiber stability. Applicants' previous patent application Ser. No. 08/274,673, now U.S. Pat. No. 5,616,689, describes the fact that physical properties of the stabilized collagen dispersion, such as strain-thinning behavior (affecting extrusion of the material though a conduit such as a needle) and gel elasticity of the product are affected by the sodium hydroxide treatment. Thus, depending on the end use for the collagen fibers, it can be critically important that the stability of the collagen fiber assembly be controlled so that physical properties of the fibers are maintained despite treatment with sodium hydroxide to inactivate prions and other infectious agents.

2. The Inactivation of Prions

As referenced in the prior art, the World Health Organization has recommended the treatment of animal tissues with 1.0M sodium hydroxide at 20° C. for a time period of at least one hour for purposes of inactivation of prions (also called "slow acting viruses").

A detailed study has been conducted under the direction of applicants, to determine whether solutions of connective tissue molecules, atelopeptide collagen molecules in particular, can be treated with sodium hydroxide at reduced concentrations (below 1.0M), temperatures, and time periods to reduce the effect on collagen fiber stability, while providing an acceptable inactivation of prions.

The study was conducted to measure the level of inactivation of hamster scrapie strain 263K infectivity that is achieved in the presence of soluble collagen at a concentration of 2.25 mg/ml after 60 minutes of exposure at 20° C. to 1.0M (1.0N); 0.5M; and 0.25M sodium hydroxide, followed by 5 minutes of neutralization with 3.0M; 1.5M; or 0.75M hydrochloric acid, respectively. Published work of Brown, P.; Rohwer, R. G.; and Gajdusek, D. C., "Newer data on the inactivation of scrapie virus or Creutzfeldt-Jakob disease virus in brain tissue", *J. Infect. Dis.*, 153: 1145–1148 (1986) indicated that 1.0M sodium hydroxide provided more than required reserve capacity for the inactivation of scrapie infectivity in brain homogenate, while 0.1M sodium hydroxide is close to the lower limit at which significant inactivation occurs. Such data was not available for the efficacy of such treatment of atelopeptide collagen in solution. The 263K strain of scrapie was selected for the inactivation study in solutions of atelopeptide collagen, as it is the shortest incubation model known, incubation time being dose dependent, with the limiting dilution requiring 240 to 360 days.

A detailed description of each experimental protocol used in the study for inactivation of the 263K strain of scrapie is not presented herein, as many of the techniques are used in the art and are well documented. However, the methodological principles are described below, as are particular factors of interest in the present study.

A. Methodological Principles

Quantal titration of the hamster-adapted scrapie agent in golden Syrian hamsters after intracerebral inoculation is the fastest and most quantitative assay so far developed for a transmissible spongiform encephalopathy agent.

The scrapie agent does not grow in tissue culture in a way that is useful for titration. Therefore, the agent must be titered by direct inoculation into live animals, which must then be observed for the development of disease. Since scrapie is a prion ("slow virus") disease, the observation period is lengthy. In the case of the hamster-adapted 263K strain of scrapie, the shortest incubation model known, incubation time is dose dependent, with the limiting dilution requiring 240 to 360 days.

Quantitation is achieved by analyzing a ten-fold serial dilution of the sample for the dilution that kills only 50% of the animals inoculated. At least four hamsters are inoculated intracerebrally with each dilution in the series. Lower dilutions containing higher concentrations of agent will kill all of the inoculated hamsters. High dilutions will, after a point, contain no agent and will kill none of the inoculated hamsters. The transition from dilutions that kill to those that do not is called the "breakpoint" in the titration. The inverse of the dilution at breakpoint is a rough estimate of the titer of the agent.

A better estimate can be calculated statistically if the breakpoint is bounded by at least one dilution in which all of the inoculated animals are killed, and one in which none of them are killed. Since this point cannot be known in advance for a sample of unknown titer, it is usually best to inoculate the entire dilution series and carry the dilutions beyond the point where even the highest titer sample could not cause disease.

The precision of the titer is a function of the number of animals inoculated at each dilution. For four animals, the resultant titer has uncertainties of approximately one factor of ten.

High dilutions of challenge into the test article minimize the effects of contaminating brain tissue from the challenge homogenate. Low dilutions of challenge stock into the test article increase the dynamic range of the assay. If the test article is to be diluted during processing, this must be compensated by using a higher initial titer of challenge infectivity.

Since the titer of the hamster agent in brain can be as high as $10^{11}$ per gram, a one percent suspension can contain as much as $10^9$/ml. The maximum volume that can be inoculated is 0.05 ml so the maximum titer that can be inoculated is $5 \times 10^7$. This value also establishes the maximum dynamic range of the assay. To cover this range, 8+1 serial ten-fold dilutions are required.

Each dilution is inoculated into four hamsters. Hamsters receiving the highest titer inoculum develop disease within 60 days. Most of those receiving a limiting dose develop disease by 240 days. Stragglers occur and are probably animals that, while receiving the inoculum intracerebrally, contracted the disease from a peripheral site due to transport of the agent in blood or in the collagen in solution before infection. The incubation time of the disease provides a rough estimate of titer, and can be used to monitor the progress of the titration. For this purpose, and because all other data must be related back to the challenge titer, the challenge titer is measured in duplicate. The statistical precision of the assay can also be improved by inoculating additional animals in that region of a dilution series where a breakpoint is expected if it can be predicted.

B. The Present Prion Inactivation Study

1) Safety Precautions: All activities involving scrapie infectivity were conducted in the animal biosafety level III facility of the Baltimore VA Medical Center Research according to the standard operating procedures for that facility. The activities were carried out by Dr. Robert G. Rohwer, Ph.D., based on an experimental protocol agreed to by the applicants and Dr. Rohwer.

2) Preparation Of Scrapie Infectivity Challenge: The infectivity challenge was prepared from hamster brains pooled from animals sacrificed late in the clinical phase of the disease when brain titers were highest. Brain homogenate was prepared using ultrasonication.

3) Titration Of The Scrapie Agent Challenge Stock: The challenge stock was titered in duplicate using two completely separate dilution series of the same 6 ml aliquot of the challenge stock. This increased the statistical significance of the challenge stock titer which, because it was the denominator in all subsequent calculations of clearance values, was the most critical measurement.

Eight animals were used at the $10^{-8}$ and $10^{-9}$ dilutions to further increase the statistical significance of the result.

4) Sodium Hydroxide Inactivations: See Table I, below, for a summary of volumes and concentrations at each step of the procedure. Each experiment was conducted separately.

c) 0.25M Sodium Hydroxide

One 50 ml tube containing 18 ml of 10% scrapie brain homogenate in PBS pH 7.2 was thawed, and 18 ml of the 10% SBH was added to 102 ml of 3.97 mg/ml collagen in solution, which was mixed as described above. This produced a 1.5% suspension of brain homogenate that, when diluted with 60 ml of 0.75N sodium hydroxide, yielded a final concentration of the infectivity spike of 1% and 2.25 mg/ml soluble collagen.

ii) Preparation of the Sodium Hydroxide-Treated Spiked Collagen Solutions:

a) The spiked collagen suspension and sodium hydroxide inactivant were equilibrated at 20° C. by placing the sodium hydroxide in a 20° C. water bath and maintaining the spiked collagen at 20° C. by connection to a recirculating bath.

b) To prepare each of the three sodium hydroxide-treated spiked collagen solutions, the appropriate amount of the 1.0M, 0.5M, or 0.35M sodium hydroxide was pumped into the stirred, spiked collagen solution at a rate of approximately 4 ml per minute, while the mixture was maintained

TABLE I

VOLUMES AND CONCENTRATIONS OF REACTANTS IN THE NAOH INACTIVATIONS
Scheme D: Hold all variables constant; collagen at 2.25 mg/ml

INACTIVATION

| Experiment | Formulation of challenge | | | Concentrations in challenge | | | Inactivant | | final composition of inactivation mix | | | |
|---|---|---|---|---|---|---|---|---|---|---|---|---|
| Final NaOH conc. | 10% SHB mls | Soluble Collagen mls | Soluble Collage conc. | Volume mls | % Conc. SHB | Collagen Conc. mg/ml | Conc. NaOH added N | Volume of NaOH | Total Volume mls | Conc. NaOH N | Conc. Collagen mg/ml | % Conc. SHB % |
| 1N | 18 | 102 | 3.97 | 120 | 1.50 | 3.38 | 3.00 | 60 | 180 | 1.00 | 2.25 | 1.00 |
| 0.5N | 18 | 102 | 3.97 | 120 | 1.50 | 3.38 | 1.50 | 60 | 180 | 0.50 | 2.25 | 1.00 |
| 0.25N | 18 | 102 | 3.97 | 120 | 1.50 | 3.38 | 0.75 | 60 | 180 | 0.25 | 2.25 | 1.00 |

NEUTRALIZATION

| Experiment | Addition of PBS and HCl | | | | | Final concentrations | | | | |
|---|---|---|---|---|---|---|---|---|---|---|
| Final NaOH conc. | Conc. PBS added | Volume PBS added | Conc. HCl added N | Volume of HCl mls | Final Volume mls | % Conc. SHB | Collage Conc. mg/ml | PBS Conc. | NaCl N Conc. acid/base | NaCl N Conc. plus PBS |
| 1N | 10x | 26.67 | 3.00 | 60 | 266.67 | 0.68 | 1.52 | 1.00 | 0.68 | 0.82 |
| 0.5N | 10x | 26.67 | 1.50 | 60 | 266.67 | 0.68 | 1.52 | 1.00 | 0.34 | 0.48 |
| 0.25N | 10x | 26.67 | 0.75 | 60 | 266.67 | 0.68 | 1.52 | 1.00 | 0.17 | 0.31 |

*The ionic composition of PBS is: 9.2 mM PO4(3−); 154 mM Na⁺; 3.84 mM K⁺; 140.6 mM Cl
PBS is presumed to add 140.6 mM NaCl to the final mixture.

i) Preparation Of The Scrapie Agent Spiked Materials:
  a) 1.0M Sodium Hydroxide One 50 ml tube containing 20 ml of 10% scrapie hamster brain homogenate (SBH) in PBS pH 7.2 was thawed, and 18 ml of the 10% SBH was added to 102 ml of 3.97 mg/ml collagen in solution, which was mixed by constant stirring in a 500-ml stainless steel tempering beaker, maintained at 20° C. by connection to a recirculating bath. This produced a 1.5% suspension of brain homogenate that, when diluted with 60 ml of 3.0M sodium hydroxide, yielded a final concentration of the infectivity spike of 1% and 2.25 mg/ml soluble collagen.

b) 0.5M Sodium Hydroxide

One 50 ml tube containing 20 mls of 10% SBH in PBS pH 7.2 was thawed, and 18 mls of the 10% SBH was added to 102 ml of 3.97 mg/ml collagen in solution, which was mixed as described above. This produced a 1.5% suspension of brain homogenate that, when diluted with 60 ml of 1.5M sodium hydroxide, yielded a final concentration of the infectivity spike of 1% and 2.25 mg/ml soluble collagen.

at 20° C. Each mixture was then incubated at the 20° C. for a sixty (60) minute period under constant stirring. After the 60 minute incubation/inactivation period, each mixture was connected to a 4° C. recirculation bath, followed by the addition a neutralization composition to the mixture. The neutralization composition consisted of 26.7 ml of 4° C. 10× Dulbeccos's Phosphate-Buffered Saline (D-PBS) (GibcoBRL 310-4200) combined with 55 ml of hydrochloric acid of the proper molarity (3.0M, 1.5M, or 0.75M, depending on the concentration of sodium hydroxide in the mixture).

The resulting sodium hydroxide-treated spiked collagen solutions obtained for the 1.0M sodium hydroxide-treated, 0.5M sodium hydroxide-treated, and 0.25 sodium hydroxide-treated materials were: 1) a 267 ml mixture at 1.52 mg/ml collagen, 0.2 mM phosphate, 820 mM sodium chloride and 0.68% brain homogenate; 2) a 267 ml mixture at 1.52 mg/ml collagen, 9.2 mM phosphate, 480 mM sodium chloride and 0.68% brain homogenate; and 3) a 267 ml mixture at 1.52 mg/ml collagen, 9.2 mM phosphate, 310 mM sodium chloride and 0.68% brain homogenate, respectively.

5) The Inoculation of Hamsters: Weanling male golden Syrian hamsters were purchased from a commercial supplier and held in quarantine for determination of their condition. Those found to be in acceptable condition were inoculated 3 to 5 weeks after receipt. Thirty-six (36) animals each were inoculated with the 1.0M sodium hydroxide-treated mixture described above. Thirty-six (36) animals each were inoculated with the 0.5M sodium hydroxide-treated mixture described above. Thirty-six (36) animals each were inoculated with the 0.25M sodium-hydroxide-treated mixture described above. In addition, Table II below shows a summary of the challenge stock titration animals inoculated.

TABLE II
SUMMARY OF CHALLENGE STOCK TITRATION

| Serial Dilution | Challenge Inoculum in duplicate | |
|---|---|---|
| $10^{-1}$ | 4 | 4 |
| $10^{-2}$ | 4 | 4 |
| $10^{-3}$ | 4 | 4 |
| $10^{-4}$ | 4 | 4 |
| $10^{-5}$ | 4 | 4 |
| $10^{-6}$ | 4 | 4 |
| $10^{-7}$ | 4 | 4 |
| $10^{-8}$ | 8 | 8 |
| $10^{-9}$ | 8 | 8 |
| $10^{-10}$ | 4 | 4 |
| Subtotals | 48 | 48 |
| Sentinels | 4 | |
| GRAND TOTAL | 100 | |

6) Scoring For Disease: Animals were checked twice weekly for signs of scrapie disease and were scored for the presence of a startle response, "S"; gait disturbance, "G"; hyperactivity, "H"; wobbling gait/head bobbing, "W"; failure to rear, "R"; prostration, "P"; and death, "D". Intercurrent illness, fighting, injury or any other unusual occurrence was noted. Animals scored as positive for any of the above signs were subsequently checked daily for progression of disease. Animals were killed by $CO_2$ anoxia once clear and consistent signs of scrapie were evident, i.e., they presented with wobbling gait, head bobbing, and reluctance to rear. The ultimate determination of titer depends critically upon the ratio of affected and unaffected animals at the breakpoint dilution. For that reason, all animals at the breakpoint, and one at one dilution above and below the breakpoint, were checked for histological signs of the disease as confirmation of their clinical state. Unaffected animals will be sacrificed at 6 and 12 months of incubation for histopathological examination.

C. Results of the Inactivation Study

All three sodium hydroxide-treated spiked collagen solutions failed to produce any diseased animals within the time period, indicating that all three sodium hydroxide treatment conditions inactivated at least 5 logs of high titer infectivity.

FIG. 4 shows the response of animals which were inoculated with non-sodium hydroxide-treated collagen solutions spiked with the scrapie-infected brain homogenate. The time post-inoculation of the first clinical sign of scrapie observed in each individual animal is plotted against the dilution of the inoculum administered to that animal. Where symbols would overlap, they have been offset slightly so that it can be seen how many animals are actually involved at a given locus. The dotted line 402 at $6.8\times10^{-8}$ on FIG. 4 represents the position of the first dilution in all three of the sodium hydroxide experiments. If agent survives the sodium hydroxide treatments, the first animals affected would be at this dilution and their data points would fall on this line. No such animals were affected. The solid line 404 and dashed line 406 through the data points regress the two challenge titrations independently to show the spread in the data.

The scatter observed in the challenge data is typical of a scrapie titration and, within that constraints, the two determinations of the challenge are acceptably consistent. At 102 days, there had been no indication of scrapie disease among the animals receiving sodium hydroxide-treated material from any of the three experiments. This represents at least 5 logs of clearance. The analysis indicates that the six highest dilutions of all three of the sodium hydroxide experiments contain no infectivity. Should animals from the sodium hydroxide experiments contract scrapie, they would first do so at the $6.8\times10^{-3}$ dilution. However, the maximum titer that such a late onset could represent is given by the dose response of the challenge. The extension of the dose response curve to the maximum possible titer ($10^{11}$, based on the past experience of Dr. Rohwer and others) shows that there could be no more than three logs of infectivity remaining in the sample, as illustrated by line 408 on FIG. 4. Transferring extended line 408 and information back to the hypothetical data point, as shown at 410, it is seen that dilutions below $10^{-5}$ will not be infectious, illustrated at 412 on FIG. 4.

3. Effect Of Sodium Hydroxide Treatment On Collagen Fiber Stability

Based on the data presented above for the inactivation of prions (hamster scrapie strain 263K) contained in solutions of atelopeptide collagen, applicants have determined that sodium hydroxide concentrations above 0.25M sodium hydroxide (and perhaps at even lower concentrations) are adequate for inactivation. However, applicants had shown that contact of collagen solutions with 1.0M sodium hydroxide for a period of 60 to 70 minutes at a temperature of about 20° C. affected the collagen molecules, resulting in unstable fibers. The issue then became whether there were sodium hydroxide concentrations capable of prion inactivation which did not significantly affect the collagen molecules in solution.

The collagen solutions used in the present examples (preferred embodiments) are derived from bovine hides, although collagen may be obtained in commercially useful amounts from the connective tissues of a variety of domesticated animals, such as cattle, swine, sheep, and goats, for example. Native collagen fibers are composed of regularly arranged subunit structures referred to as collagen molecules. A collagen molecule typically is about 3000 Å long and 15 Å in diameter. The long rigid rod-like structure consists of three polypeptide chains wound together in a triple helical configuration. Typically, two of the constituent chains are identical in composition and the third is different. A characteristic distribution of amino acid residues along the length of any given polypeptide strand, wherein repeating triplets contain glycine at every third position, favors the formation of a helical configuration. The individual collagen molecules assemble into fibrils (subassemblies) which associate to form fibers (assemblies). The associated fiber assemblies can become disassociated upon exposure to high salt concentrations and to active agents such as lidocaine, as we have observed above.

The bovine collagen used in the examples (preferred embodiments) herein was obtained from hides. The hides were cleaned physically to remove some of the non-collagen materials, such as hair, fat, carbohydrates, mucopolysaccharides, and the like. The hides were then subjected to commutation (grinding and high speed shearing) to enhance subsequent processing, such as purification, and to facilitate the enzymatic removal of the telopeptide region of the collagen molecule (which has undesired immunogenic properties).

Coarsely divided connective tissues were swollen in aqueous acidic solutions under non-denaturing conditions. Further dispersion was achieved through extensive wet grinding, to facilitate enzyme access to the native collagen. Dilute acid solutions at low temperatures are employed to minimize denaturation. Suitable acids are acetic, malonic or lactic acids, or other lyotropic carboxylic acids having pK values from about 2 to about 5 at 25° C. Concentrations of acid in the dispersion medium can range from about 0.01M to 1.0M, and temperatures may vary from about 4° C. to about 25° C. The dispersion which was obtained by treatment with acid was a viscous dispersion containing native collagen microaggregates and a small amount of native collagen in solution.

The viscous product was subjected to enzymatic treatment to remove the telopeptides and to produce soluble atelopeptide collagen. Various proteolytic enzymes may be employed which preferentially attack the telopeptides, while leaving the major portion of the molecule intact. Illustrative enzymes include pepsin, trypsin and pronase, for example. See U.S. Pat. Nos. 3,131,130 and 3,530,037.

The preferred enzyme is pepsin, which was used in combination with an acidic solution, generally at a pH of about 2 to 4. The concentration of the enzyme varies from about 0.001 to about 10 weight percent based on the weight of collagen present. The collagen protein concentration generally varies from about 0.5 g/l to about 10 g/l. Preferably, the acidity is provided by a carboxylic acid in a concentration of about 0.01M to about 1.0M. If necessary, the pH was adjusted by the addition of a mineral acid, hydrochloric acid. The enzymatic treatment was generally carried out over temperatures ranging from about 0° C. to about 30° C. over a time period ranging between two days and two weeks, with progress monitored periodically until substantially complete solubilization of the collagen was achieved.

The resulting solution was treated to separate the soluble atelopeptide collagen from insoluble collagen, enzymes, residual amino acids, and the telopeptide units which had previously separated from the collagen molecules. Primarily, the treatment involved separations, precipitations, and dialysis against various solutions of different ionic strengths. Moderate temperatures were employed, normally from about 4° C. to about 30° C., and salt solutions of various ionic strength or concentration were employed, generally from about 0.01M to about 3.5M, depending upon the particular salt. Ionic strengths were usually about 0.01 to 3.5.

Conveniently, the solution was treated with an alkaline material, e.g., sodium hydroxide, to raise the pH of the solution to at least about seven, to inactivate the enzyme. After inactivating the enzyme, non-solubilized contaminants which had been precipitated during the inactivation treatment were filtered off to yield a filtrate which contains collagen in solution.

The collagen in solution was passed through a bed of celite and subsequently processed via ultrafiltration to provide a purified, clear solution containing about 3 mg/ml of atelopeptide collagen. This concentrated solution of collagen is relatively free of higher aggregates, and is referred to as concentrated submicron filtrate (CSF). It was this CSF which was treated with sodium hydroxide in the preferred embodiments described herein, for purposes of inactivation of prions and other infective agents.

After the sodium hydroxide-treatment and subsequent neutralization with hydrochloric acid, the mixture is concentrated to 3.0 mg/ml protein concentration and diafiltered at constant volume with 0.013M hydrochloric acid to reduce the residual salt concentration to less than 20 mM. The collagen solution is then further purified through a batch cation exchange column in a two-stage elution with HCl (pH 2.0) to produce a collagen solution at 0.3 mg/ml protein. The eluate is then concentrated to about 2.5 to 3.0 mg/ml protein by ultrafiltration and diafiltered with at least 2.5 volumes of 0.013M HCl. This concentrated, purifed collagen solution at pH 2.0 is then precipitated by the addition of appropriate buffers and formulated for testing.

From a prion deactivation perspective, it is preferable to treat a solution of collagen with sodium hydroxide rather than to treat precipitated fibers in a dispersion. The soluble collagen molecule and any beginning fibrils which are in solution are dissociated to permit maximum availability of any infectious agents which may reside in or be trapped within fiber structures. The collagen triple helix is too tightly wound (1.5 nm diameter) for viruses and prions (to the extent that they are known) to reside within the collagen molecule. Therefore, such virus or prion would be present either in the solution or absorbed onto the surface of a collagen molecule. In the soluble environment, where collagen fibers are dissociated into collagen molecules, there is no mass transfer barrier which requires the sodium hydroxide to diffuse through solids (assembled fibers) to reach the infectious agents on the surface of collagen molecules.

It has been discovered that it is possible to treat solutions of collagen molecules for the inactivation of prions in a manner such that the collagen molecule is not affected by the inactivation treatment. For example, fibers formed from solubilized atelopeptide collagen treated with sodium hydroxide can exhibit the same behavior in terms of melting temperature, opacity upon examination by spectrophotometric techniques, stability in the presence of solvents and agents which cause dissociation, and rate of fiber formation when compared with collagen which has not been treated with sodium hydroxide.

It has been discovered that, in the treatment of collagen for the inactivation of prions and other infective agents to obtain at least 5 logs of protection, the following steps do not significantly affect the formation of stable collagen fibers, based on DSC curve data and opacity measurements for formulated collagen at 35 mg/ml:

a) placing the collagen in solution, whereby the surface area of the connective tissue to be treated exposes said prions and infectious agents for treatment; and b) contacting the solution of collagen molecules with sodium hydroxide so that the concentration of sodium hydroxide in said solution or dispersion is 0.7M or less for a time period of about 30 minutes or less at a temperature of about 25° C. or less.

At 25° C. and higher, for concentrations of sodium hydroxide greater than about 0.7 Molar, the ability of the collagen molecules to form subassemblies is significantly altered, even though the time period of exposure is as low as 5 minutes.

It is preferable to maintain the sodium hydroxide concentration of the collagen treatment solution at about 0.5 Molar and lower (at about 25° C.), since sodium hydroxide concentrations in this range are capable of deactivating prions within a time period of 60 minutes or less, reduce the heat transfer problems upon neutralization of the sodium hydroxide, and have been demonstrated to have minor to no effect upon the ability of the treated collagen molecule to form stable fibers.

EXAMPLES 4–7
Various Molar Concentrations of Sodium Hydroxide Treatment

The following process was used in the treatment of collagen solutions with sodium hydroxide. Several different sodium hydroxide concentrations were evaluated. In particular, individual collagen solutions were treated using the following concentrations of sodium hydroxide: 0.75M, 0.5M, 0.35M, 0.25M, and 0.1M. To independently evaluate the effects of the sodium hydroxide treatment, independent of other processing variables as much as possible, experiments were carried out in which a large quantity (8 times the volume of collagen solution) of cold ($\approx 4°$ C.) water was added at the end of the sodium hydroxide treatment period, to reduce the sodium hydroxide concentration to a low level and reduce the reaction temperature, thereby enabling neutralization of the sodium hydroxide without further significant effect on the collagen molecules.

In particular, 250 g of bovine atelopeptide collagen (3.0 mg/ml protein in an aqueous base solution, pH 2.0) was brought up to the sodium hydroxide concentration to be tested (0.75M, 0.5M, 0.35M, 0.25M, or 0.1M) by the addition of 1M sodium hydroxide over a 15 minute period at a temperature of less than 20° C. The addition of sodium hydroxide was made using a peristaltic pump and the mixture was stirred throughout the addition. The mixture was then held at 20° C. for 60 minutes (for all sodium hydroxide concentrations except for 0.75M, which was held at 20° C. for 30 minutes). At completion of the sodium hydroxide treatment, 2000 ml of cold water ($\approx 4°$ C.) was added quickly (over a 1 minute time period) to quench the sodium hydroxide reaction. The diluted mixture was stirred for approximately 3 minutes and then neutralized with 1M hydrochloric acid over a 15 minute time period. The mixture (pH 2.0) was concentrated to approximately 3.0 mg/ml protein using a Filtron Ultrasette Omega series Polyethersulfone membrane, and then diafiltered at constant volume against 4 volumes of 0.013M hydrochloric acid. The addition of a large volume of cold water reduced the sodium hydroxide to negligible concentrations and the temperature to about 6° C. Subsequently, the collagen in solution at 3.0 mg/ml was precipitated at about 17° C. by the addition of 0.2M Disodium Phosphate buffer adjusted to a pH of 11.2 using sodium hydroxide. The volumetric ratio of collagen solution to buffer was 9:1. The precipitate produced contained a fibrous collagen protein concentration of approximately 2.7 mg/ml, at pH 7.0–7.4. The precipitate was concentrated by centrifugation to a protein content in excess of 35 mg/ml.

The precipitated fibers were formulated to a concentration of 35 mg/ml in PBS buffer with 3 mg/ml of lidocaine present. Specifically, the centrifugate was formulated by dilution with a water-based solution comprising 0.02M disodium phosphate, 3 mg/ml lidocaine, and 1.3M sodium chloride, at a pH of 6.3. The resulting product comprised an aqueous dispersion containing about 35 mg/ml of fibrous collagen, 3 mg/ml of lidocaine, 0.02M disodium phosphate, and 0.13M sodium chloride, at a pH of 7.0–7.4. The lidocaine causes unstable, large, assembled fibers to disassociate into the fiber subassemblies, making clear the effect of the sodium hydroxide treatment upon fiber stability.

Since the time period of sodium hydroxide treatment for the 0.75M concentration of sodium hydroxide was 30 minutes, data for this example are presented in EXAMPLE 10, below.

EXAMPLE 4
Sodium Hydroxide Concentration 0.5 Molar

Figure 5:
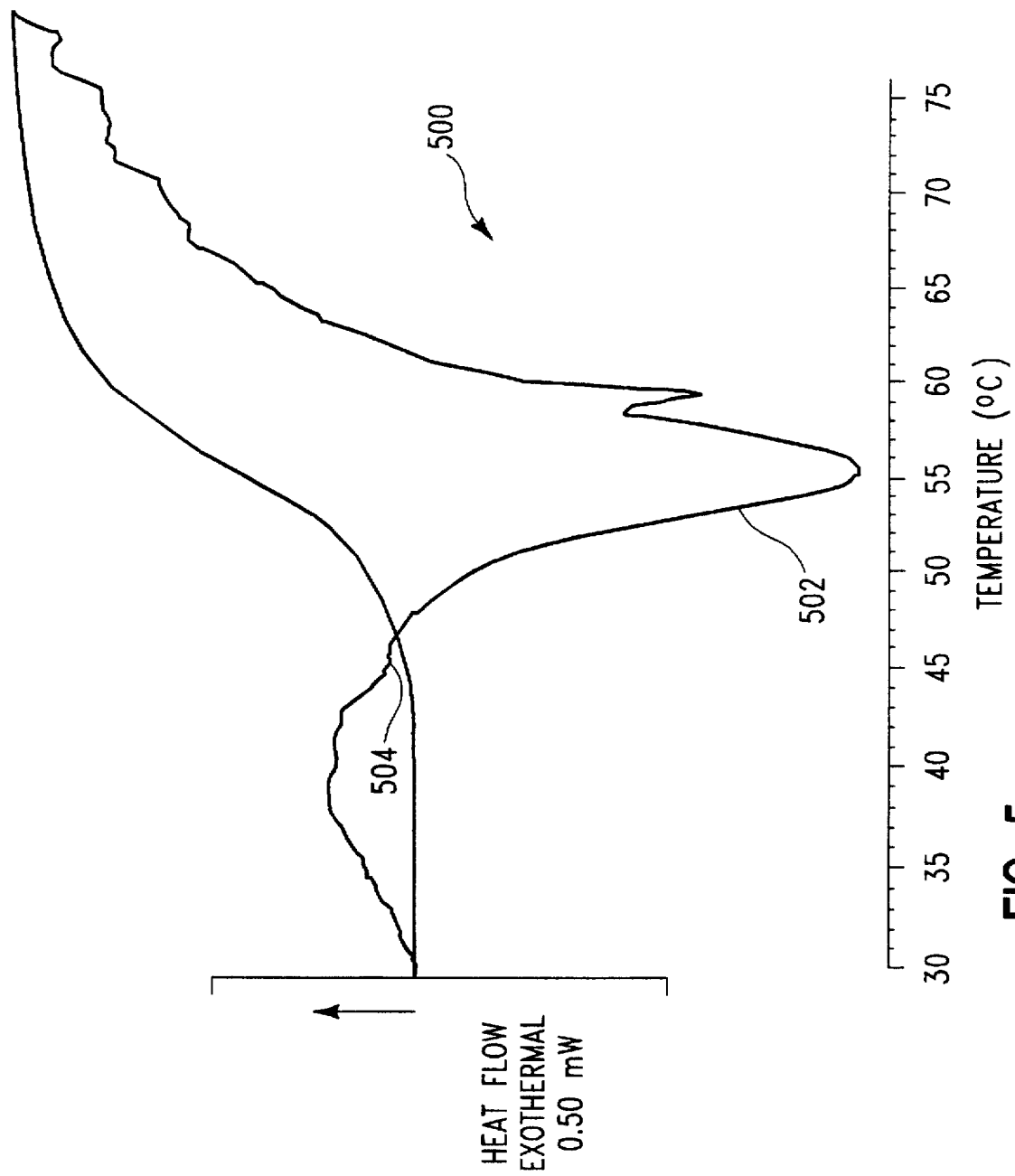
FIG. 5 illustrates the DSC curve for atelopeptide collagen fibers which were produced in the manner described for FIG. 1, except that the maximum sodium hydroxide concentration was about 0.5M.

FIG. 5 illustrates the DSC curve 500 for the atelopeptide collagen fibers produced when the collagen solution was exposed to 0.5 Molar sodium hydroxide at about 20° C. for a time period of about 60 minutes (and an additional 15 minutes of lower concentration during addition of the sodium hydroxide to the collagen solution). The bulk of the subassembly fibers fall under the area of curve 502 and have a melting temperature of about 55.6° C. A minor portion of subassembly fibers appears under curve 504 and exhibits a melting temperature of about 46.5° C. There is a possible third subassembly fiber group 506 having a melting temperature of about 60° C.; however, this subassembly unit is somewhat masked within the 502 subassembly portion of the DSC curve. In terms of instability of the collagen fiber, however, the main concern is the appearance of low melting subassembly groups such as 504, which appears in FIG. 5 to be a very minor component of the overall fiber composition. A comparison of the curve for non-sodium-hydroxide-treated collagen control fiber (FIG. 3) with FIG. 5 shows that the quantity of low melting subassembly groups is a similarly small portion of the collagen fiber composition in both cases. The opacity of the collagen fiber suspension for the 0.5M sodium hydroxide-treated collagen was 2.1, in comparison with 1.7 for the collagen standard fiber shown in FIG. 3. The increase in opacity is apparently due to the 0.5M sodium hydroxide-treated collagen fiber having a somewhat larger portion of subassemblies melting at 55.5° C. or higher, in comparison with the FIG. 3 control collagen. Since the main concern is the quantity of low melting subassembly groups, as described above, the 0.5M sodium-hydroxide-treated collagen solution is considered to provide a collagen fiber having acceptable stability.

EXAMPLE 5
Sodium Hydroxide Concentration 0.35 Molar

Figure 6:
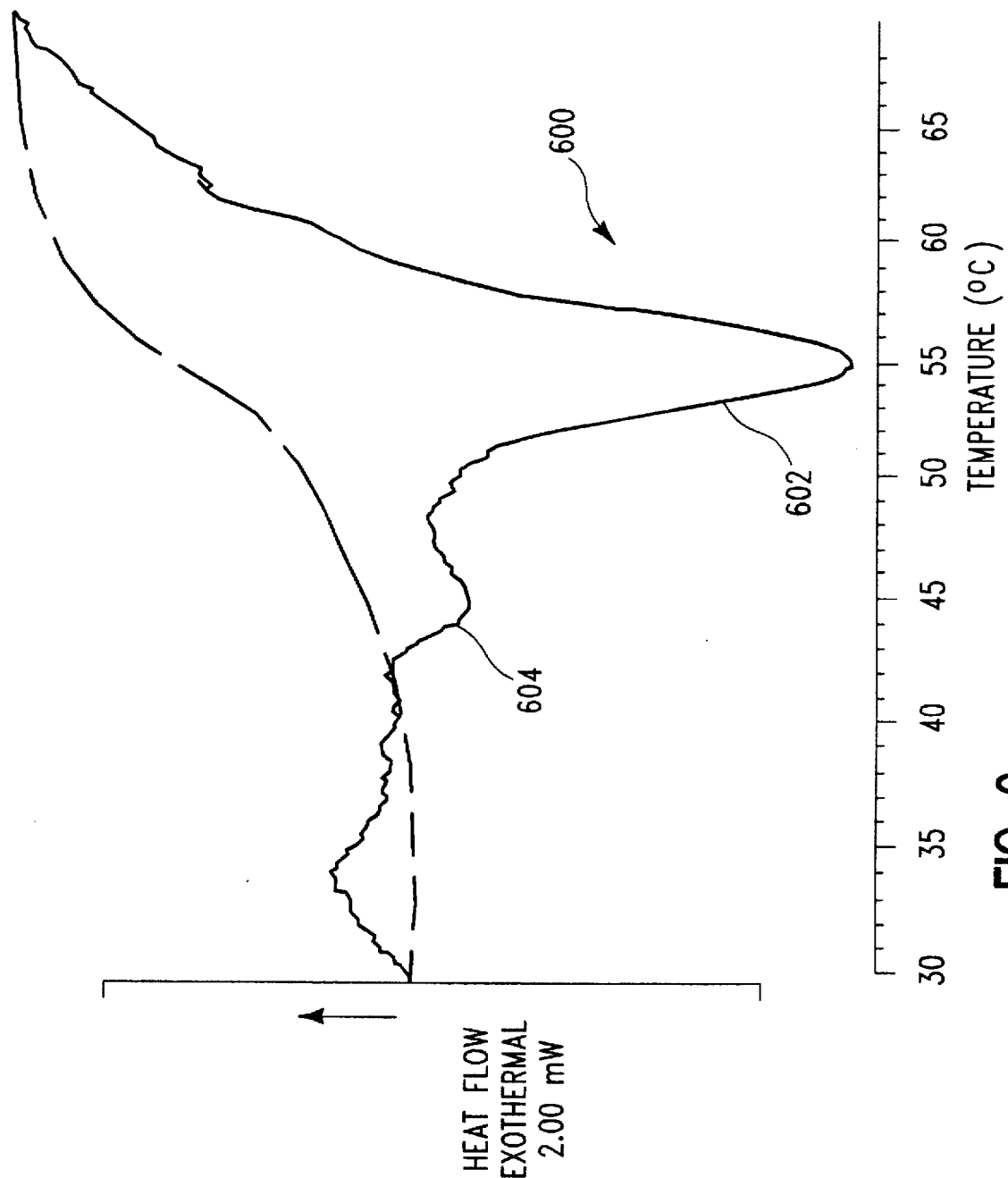
FIG. 6 shows the DSC curve for atelopeptide collagen fibers which were produced in the manner described for FIG. 1, except that the maximum sodium hydroxide concentration was about 0.35M.

FIG. 6 illustrates the DSC curve 600 for the atelopeptide collagen fibers produced when the collagen solution was exposed to 0.35 Molar sodium hydroxide at about 20° C. for a time period of about 60 minutes (and an additional 15 minutes of lower concentration during addition of the sodium hydroxide to the collagen solution). The bulk of the subassembly fibers fall under the area of curve 602 and have a melting temperature of about 54.8° C. A minor portion of subassembly fibers appears under curve 604 and exhibits a melting temperature of about 46° C. Again, there is a possible third subassembly fiber group 606 having a melting temperature of about 60° C. Again, this subassembly unit is somewhat masked within the 602 subassembly portion of the DSC curve; it is apparently reduced in quantity from the amount present in the 0.05M sodium hydroxide-treated collagen fibers. The opacity of the collagen fiber suspension for the 0.35M sodium hydroxide-treated collagen was 2.0, in comparison with 1.7 for the collagen standard fiber shown in FIG. 3. Again, the increase in opacity is apparently due to the 0.35M sodium hydroxide-treated collagen fiber having a somewhat larger portion of subassemblies melting at 55.5° C. or higher, in comparison with the FIG. 3 control collagen. Since the main concern is the quantity of low-melting subassembly groups, as described above, the 0.35M sodium hydroxide-treated collagen solution is considered to provide a collagen fiber having acceptable stability. The amount of subassembly fibers at the low melting temperature 604 on curve 600 appears to be slightly greater than the quantity observed for the 0.5 Molar sodium hydroxide concentration, but is probably within the experimental error of the method.

EXAMPLE 6
Sodium Hydroxide Concentration 0.25 Molar

Figure 7:
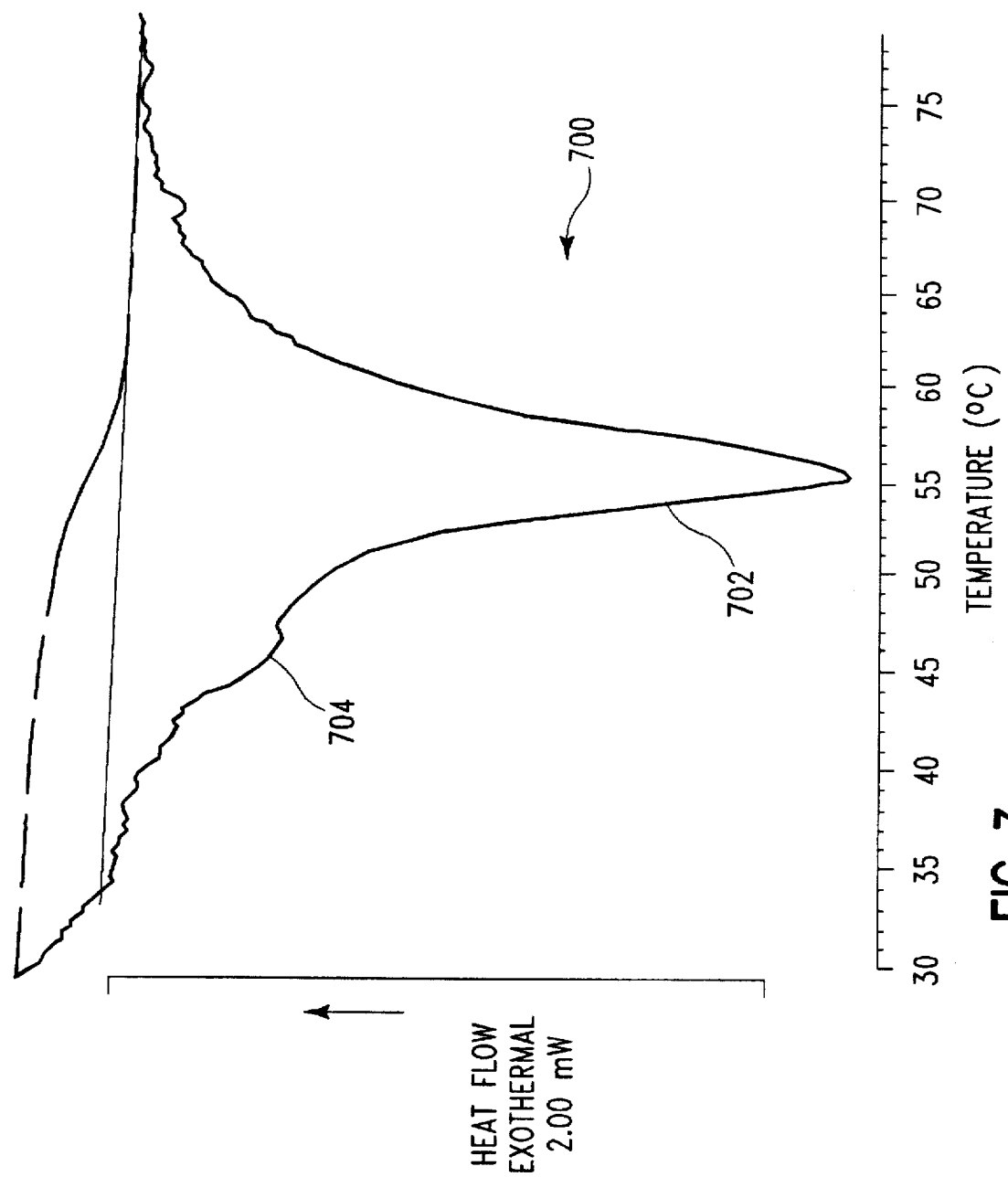
FIG. 7 shows the DSC curve for atelopeptide collagen fibers which were produced in the manner described for FIG. 1, except that the maximum sodium hydroxide concentration was about 0.25M.

FIG. 7 illustrates the DSC curve 700 for the atelopeptide collagen fibers produced when the collagen solution was exposed to 0.25 Molar sodium hydroxide at about 20° C. for a time period of about 60 minutes (and an additional 15 minutes of lower concentration during addition of the sodium hydroxide to the collagen solution). The bulk of the subassembly fibers fall under the area of curve 702 and have a melting temperature of about 55.8° C. A minor portion of subassembly fibers appears under curve 704 and exhibits a melting temperature of about 46.5° C. The opacity of the collagen fiber suspension for the 0.25M sodium hydroxide-treated collagen was 2.1, in comparison with 1.7 for the collagen standard fiber shown in FIG. 3. This increase in opacity over the collagen standard fiber suspension appears to be due to a reduction in the quantity of low-melting subassembly component in the 0.25M sodium hydroxide-treated collagen. This reduction in low melting subassembly component is probably not attributable to the sodium hydroxide treatment, but more likely due to differences in the collagen-in-solution starting material.

EXAMPLE 7
Sodium Hydroxide Concentration 0.10 Molar

Figure 8:
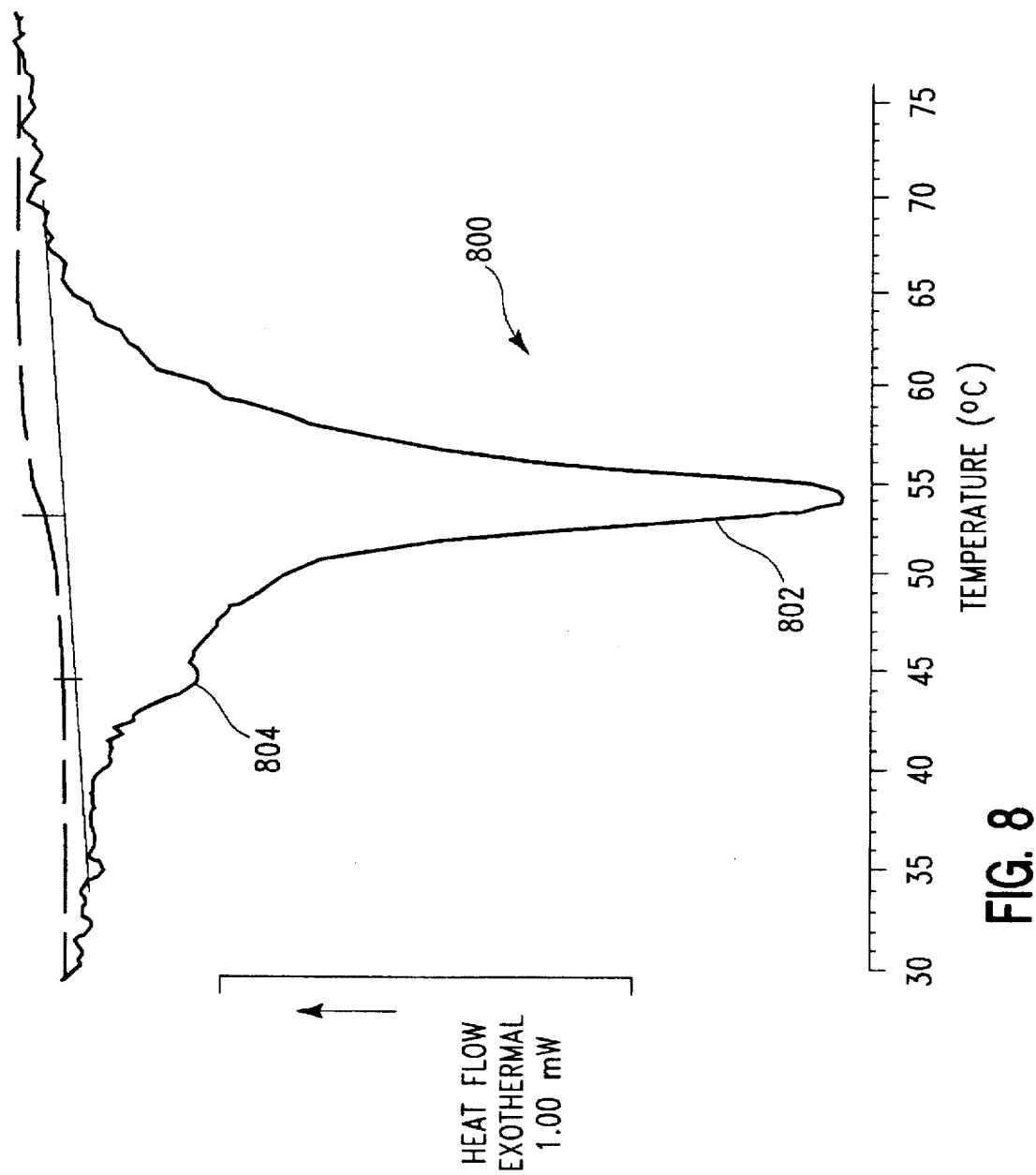
FIG. 8 shows the DSC curve for atelopeptide collagen fibers which were produced in the manner described for FIG. 1, except that the maximum sodium hydroxide concentration was about 0.10M.

FIG. 8 shows the DSC curve 800 for the atelopeptide collagen fibers produced when the collagen solution was exposed to 0.10 Molar sodium hydroxide at about 20° C. for a time period of about 120 minutes (and an additional 15 minutes of lower concentration during addition of the sodium hydroxide to the collagen solution). The bulk of the subassembly fibers fall under the area of curve 802 and have a melting temperature of about 54.2° C. A minor portion of subassembly fibers appears under curve 804 and exhibits a melting temperature of about 45.5° C. Again, there appears to be no subassembly fiber group at the 60° C. melting temperature, and the quantity of low-melting (45.5° C.) subassembly fibers is reduced from that observed for the 0.5M, 0.35M, and 0.25M sodium hydroxide-treated fibers. The opacity of the collagen fiber suspension for the 0.10M sodium hydroxide-treated collagen was 2.1, in comparison with 1.7 for the collagen standard fiber shown in FIG. 3. This increase in opacity over the collagen standard fiber suspension appears to be due to a reduction in the quantity of low melting subassembly component in the 0.10M sodium hydroxide-treated collagen. This reduction in low melting subassembly component is probably not attributable to the sodium hydroxide treatment, but more likely due to differences in the collagen in solution starting material. However, it should be mentioned that there is definitely a reduction in the amount of low-melting subassembly component as the sodium hydroxide treatment concentration is reduced from 0.35M to 0.25M to 0.10M, and the collagen-in-solution starting material was the same for all of these examples.

A comparison of the DSC curve for the control collagen fibers which were not treated with sodium hydroxide (FIG. 3) with the DSC curves for collagen fibers formed from collagen molecules treated with 0.5 Molar or lower concentrations of sodium hydroxide (FIGS. 5–8) illustrates that the effect of the sodium hydroxide treatment on the stability of collagen fibers produced from the treated collagen solution falls within an acceptable range. This acceptability is based on the amount of low-melting subassembly fiber component being comparable to that of collagen fibers which are produced from collagen molecules not exposed to sodium hydroxide treatment.

Applicants' data is limited to sodium hydroxide treatment of collagen solutions at about 20° C. At significantly higher temperatures, 30° C. for example, it might be necessary to reduce the concentration of the sodium hydroxide.

Because it would be preferable to use the most dilute concentration of sodium hydroxide which provides the desired 5 logs of protection for the inactivation of prions, various concentrations of sodium hydroxide of less than 0.7M were investigated. The lower concentrations of sodium hydroxide were investigated both for effectivity in prion inactivation and effect upon the connective tissue molecule. In the case of collagen, the effect of sodium hydroxide treatment on the collagen is particularly evidenced in the stability of collagen fibers formed from the treated collagen molecules in solution. Thus, fiber stability was used as the indicator of the effect upon the collagen molecule of exposure of the molecule to the particular sodium hydroxide concentration.

It has been discovered that, for a given sodium hydroxide concentration, at a process temperature of 25° C. or less, the following steps do not significantly affect the collagen molecules and the stability of fibers formed from such molecules, based on DSC curve data and opacity measurements for formulated collagen at 35 mg/ml, with 3 mg/ml of lidocaine and 0.13M NaCl present:

a) placing the collagen in solution, whereby the surface area of said connective tissue to be treated exposes said prions and infectious agents for treatment; and b) contacting the solution of collagen molecules at a temperature of about 25° C. or less with sodium hydroxide for the following time periods at the sodium hydroxide concentration given: 1) 0.5 Molar for 80 minutes of less; 2) 0.35 Molar for 90 minutes or less; 3) 0.25 molar for 100 minutes or less; 4) 0.1 Molar for 150 minutes or less.

EXAMPLES 8–10
Variation of Sodium Hydroxide Treatment Time

EXAMPLE 8
1.0 Molar Sodium Hydroxide, 30 Minute Treatment Time

Figure 9:
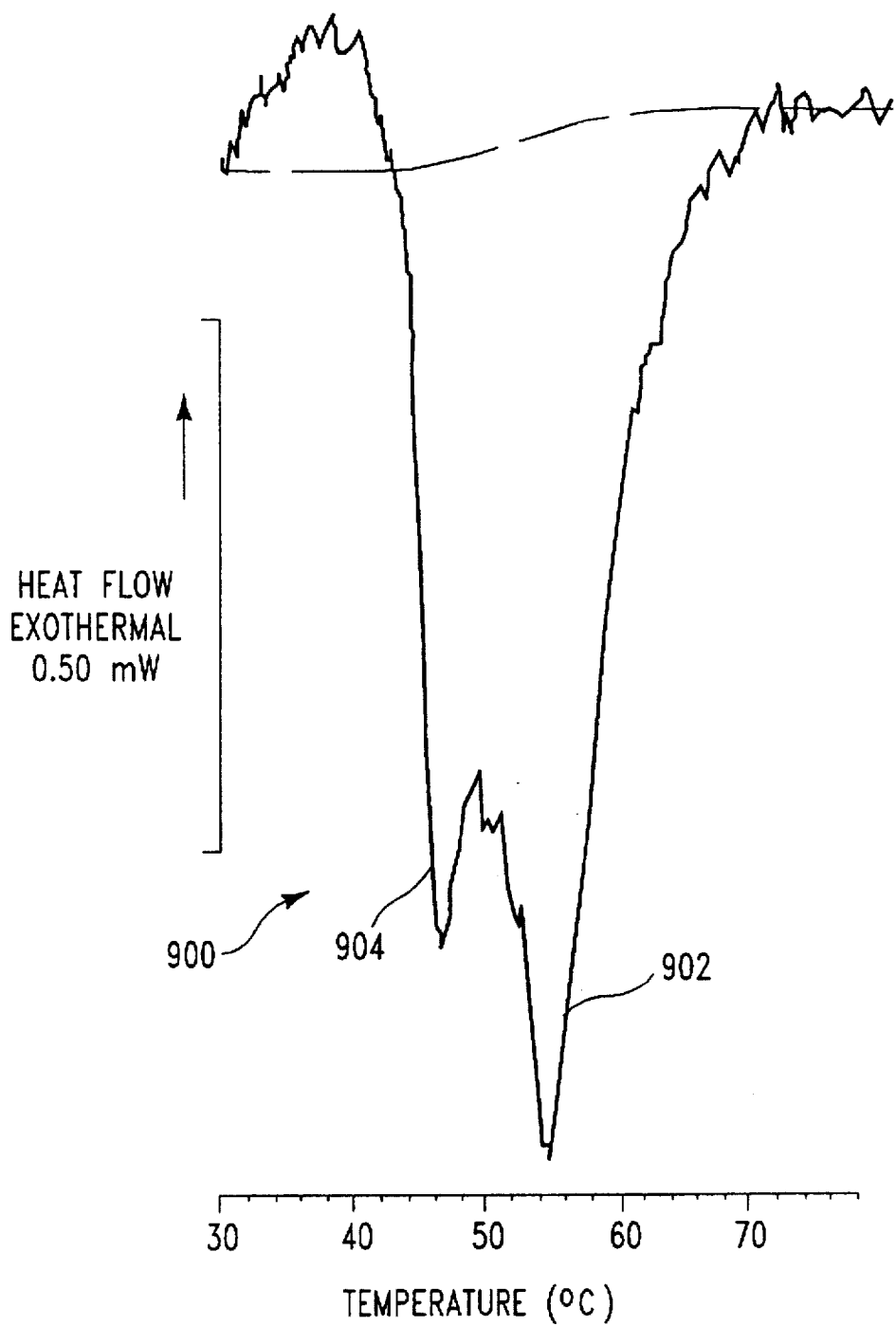
FIG. 9 shows the DSC curve for atelopeptide collagen fibers which were produced in the manner described for FIG. 1, except that the time period the collagen solution was exposed to 1.0M sodium hydroxide concentration was about 30 minutes.

FIG. 9 shows the DSC curve 900 for the atelopeptide collagen fibers produced when the collagen solution was exposed to 1.0 Molar sodium hydroxide at about 20° C. for a time period of about 30 minutes (and an additional 15 minutes of lower concentration during addition of the sodium hydroxide to the collagen solution). The majority of the subassembly fibers fall under the area of curve 902 and have a melting temperature of about 54.8° C. However, a large portion of subassembly fibers appears under curve 904 and exhibits a melting temperature of about 46.5° C.

A comparison of the DSC curve for the fibers which were treated with 1.0M sodium hydroxide (FIG. 2) for a period of about 60 minutes (plus addition time) with the FIG. 9 DSC curves for a 30 minute treatment (plus addition time) shows similar relative amounts of the high-melting and low-melting fiber subassembly units. The opacity of the collagen fiber suspension for the 30 minute treated collagen was 1.03, in comparison with 1.10 for the 60 minute treated suspension, and in comparison with 1.7 for the collagen standard fiber (nontreated) shown in FIG. 3.

EXAMPLE 9
1.0 Molar Sodium Hydroxide, 5 Minute Treatment Time

Figure 10:
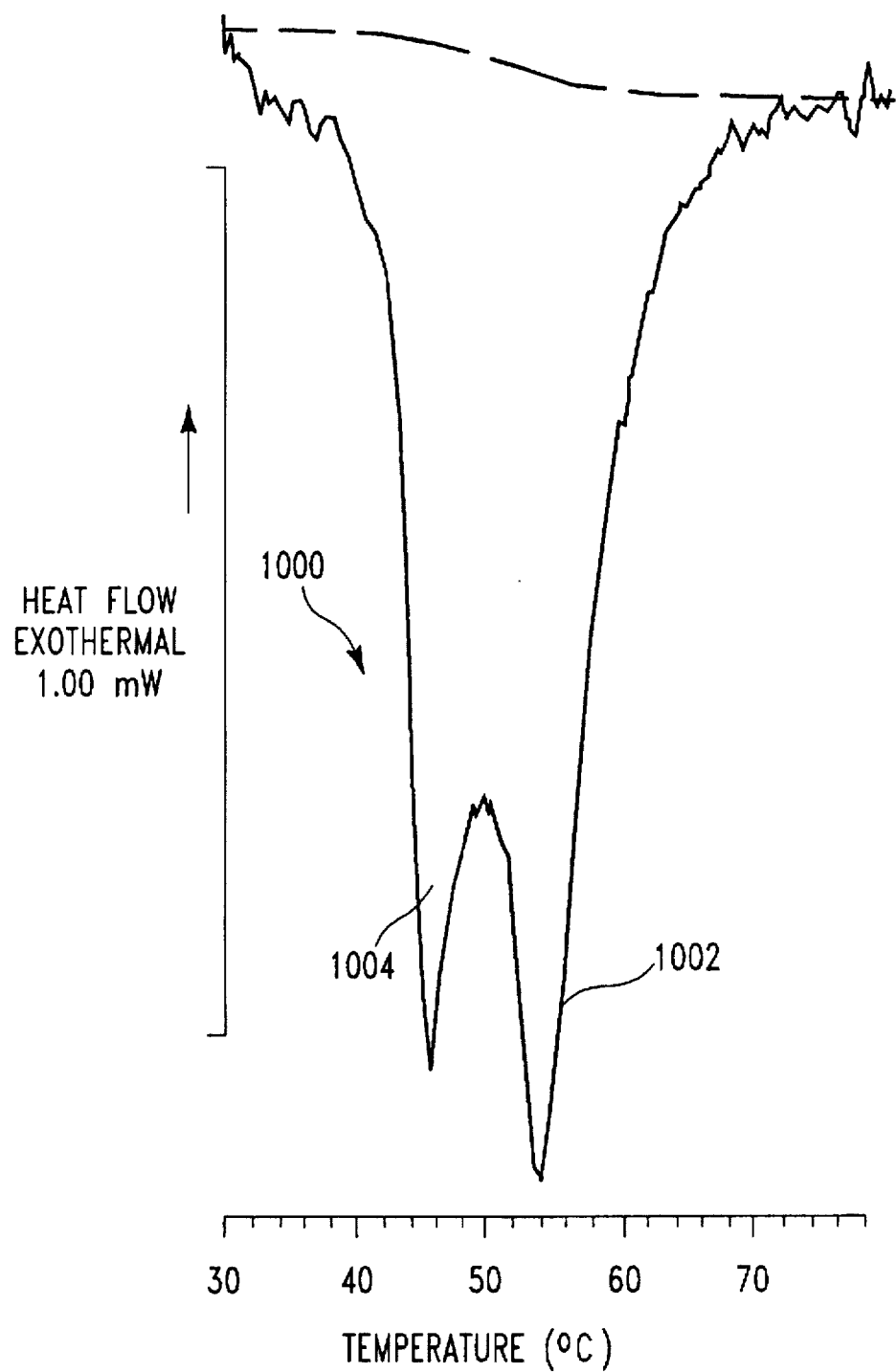
FIG. 10 illustrates the DSC curve for atelopeptide collagen fibers which were produced in the manner described for FIG. 1, except that the time period the collagen solution was exposed to 1.0M sodium hydroxide concentration was about 5 minutes.

FIG. 10 shows the DSC curve 1000 for the atelopeptide collagen fibers produced when the collagen solution was exposed to 1.0 Molar sodium hydroxide at about 20° C. for a time period of about 5 minutes (and an additional 15 minutes of lower concentration during addition of the sodium hydroxide to the collagen solution). Again, the majority of subassembly fibers fall under the area of curve 1002 and have a melting temperature of about 54° C. Surprisingly, a major portion of subassembly fibers continues to be present under curve 1004, exhibiting a melting temperature of about 46.5° C. Thus, reducing the time of exposure of the collagen-in-solution to sodium hydroxide at the 1.0M concentration from 60 minutes to 30 minutes to 5 minutes did not help reduce the amount of low melting subassembly fiber formation. The opacity of the collagen fiber suspension for the 5 minute-treated collagen was 1.05, in comparison with the 30 minute treated collagen at 1.03, in comparison with 1.10 for the 60 minute treated collagen, all of these materials exhibiting far lower opacity than the 1.7 for the collagen standard fiber (nontreated) shown in FIG. 3. This is a further indication that reduction of the treatment time to 5 minutes for the 1.0M sodium hydroxide treatment concentration was not helpful in reducing the amount of low-melting subassembly fibers (in reducing the fiber instability).

A comparison of the DSC curves for the fibers which were treated with 1.0M sodium hydroxide for a period of about 60 minutes, or 30 minutes, or 5 minutes, shows similar relative amounts of the high-melting and low-melting fiber subassembly units. This indicates that the sodium hydroxide affects the collagen molecule very rapidly at a 1.0M concentration and that, unless lower temperatures provide relief, the collagen molecules will be significantly affected at this concentration of sodium hydroxide.

EXAMPLE 10
0.75 Molar Sodium Hydroxide, 30 Minute Treatment Time

Figure 11:
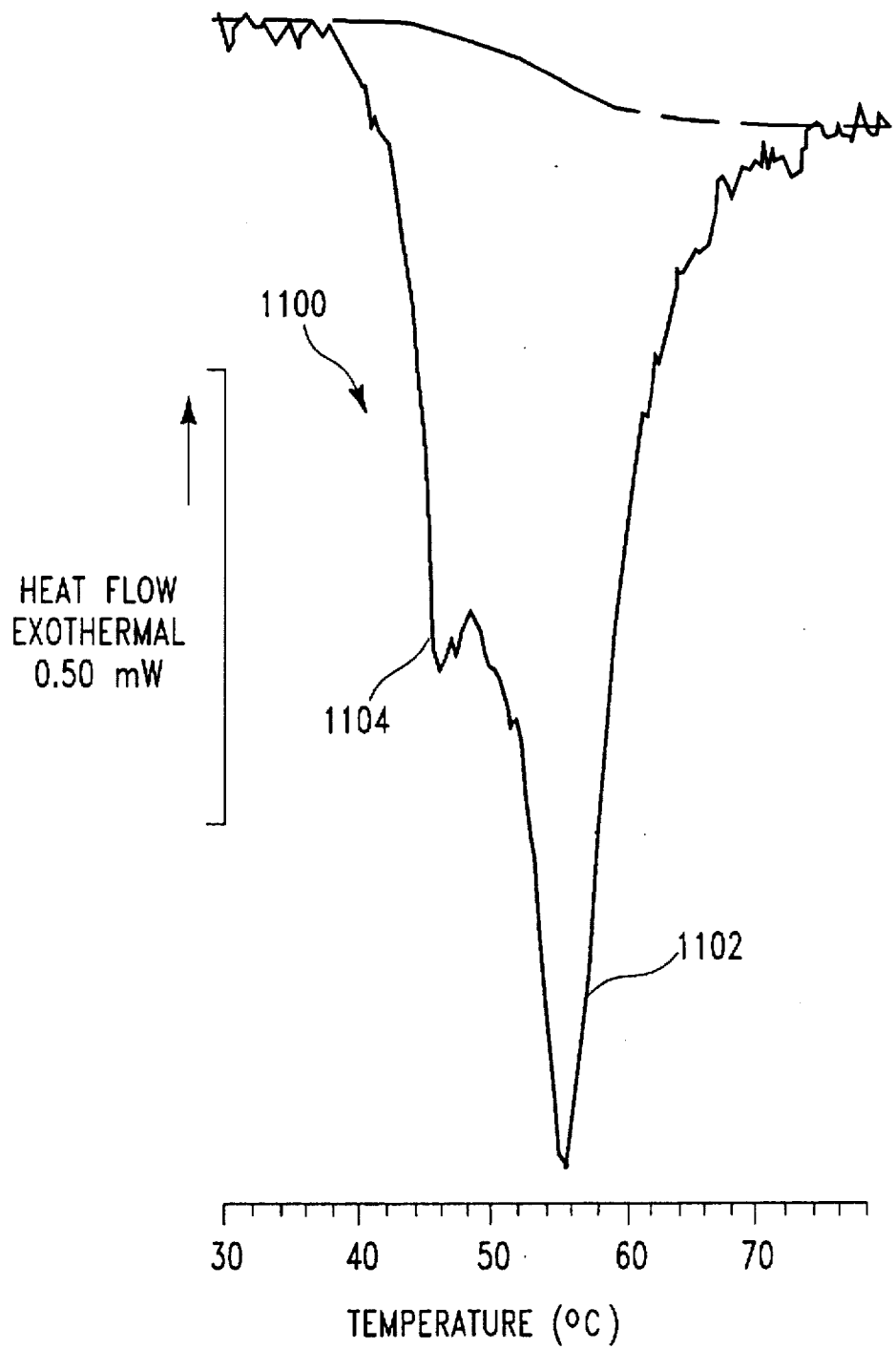
FIG. 11 illustrates the DSC curve for atelopeptide collagen fibers which were produced in the manner described for FIG. 9, except that the collagen solution was exposed to 0.75M sodium hydroxide concentration for the 30 minute time period.

FIG. 11 shows the DSC curve 1100 for the atelopeptide collagen fibers produced when the collagen solution was exposed to 0.75 Molar sodium hydroxide at about 20° C. for a time period of about 30 minutes (and an additional 15 minutes of lower concentration during addition of the sodium hydroxide to the collagen solution). The bulk of the subassembly fibers fall under the area of curve 1102 and have a melting temperature of about 55.8° C. A major portion of subassembly fibers appears under curve 1104 and exhibits a melting temperature of about 47.5° C. The opacity of the collagen fiber suspension for the 0.75M sodium hydroxide, 30 minute treatment time was 1.13, in comparison with 1.03 for 1.0M sodium hydroxide, 30 minute treatment, both of these materials exhibiting far lower opacity than the 1.7 for the collagen standard fiber (nontreated) shown in FIG. 3.

A comparison of the DSC curves for the fibers which were treated with 1.0M sodium hydroxide for a period of about 30 minutes (FIG. 9) with FIG. 11 showing the DSC curve for the fibers treated with 0.75M sodium hydroxide for the same time period indicates that the portion of subassembly fibers at the low melting temperature is reduced. However, the amount of low melting subassembly fibers present in the 0.75M sodium hydroxide-treated collagen fibers is more than twice that observed for the control collagen fibers (untreated).

A very significant decrease in the portion of subassembly is demonstrated for the 0.5M sodium hydroxide treatment, even for a sixty minute time period (FIG. 5), indicating a particular advantage below the 0.75M sodium hydroxide concentration.

In view of the above data, it is clearly possible to treat the collagen molecules in solution with a concentration of sodium hydroxide which provides at least 5 logs of protection from prion infectivity without adversely affecting the collagen molecule.

One skilled in the art can, with minimal experimentation, in view of the present disclosure, optimize the time period for a given concentration of sodium hydroxide within the ranges specified above and for concentrations intermediate to those provided.

It is not intended that the invention described herein be limited to the preferred embodiments described herein, as one skilled in the art can extend the concepts described to include the subject matter of the invention as it is limited in the claims which follow.

We claim:

1. A method for treatment of solubilized collagen to inactivate prions and other infective agents, comprising:

contacting solubilized collagen with sodium hydroxide in a liquid solution, whereby surface area of the solubilized collagen molecules is exposed, to expose prions and other infectious agents for treatment, wherein sodium hydroxide in said liquid solution ranges in concentration from about 0.1M to about 0.35M, for a time period sufficient to inactivate said prions and other infective agents, at a temperature of about 25° C. or less; wherein the collagen is capable of forming stable fibers after said inactivation.

2. The method of claim 1, wherein said time period is about 80 minutes.

3. The method of claim 1, wherein said time period is about 100 minutes.

4. The method of claim 1, wherein said time period is about 150 minutes.

5. The method of claim 1 wherein the collagen is atelopeptide collagen.

6. The method of claim 1 wherein the temperature is about 20° C.

7. The method of claim 1 wherein the temperature is about 25° C.

8. The method of claim 1 wherein the method is effective to inactivate at least 5 logs of infectivity.

9. The method of claim 1 wherein the concentration is about 0.25M to 0.35M sodium hydroxide.

10. The method of claim 1 wherein the concentration is about 0.25M sodium hydroxide.

11. The method of claim 1, wherein said time period is about 90 minutes.

12. The method of claim 11 wherein the temperature is about 20° C.

13. The method of claim 11 wherein the temperature is about 25° C.

14. The method of claim 1, wherein the concentration of sodium hydroxide in said liquid solution is about 0.1M.

15. The method of claim 14 wherein the collagen is atelopeptide collagen.

16. The method of claim 14 wherein the method is effective to inactivate at least 5 logs of infectivity.

17. A method of inactivating prions in a collagen material, comprising a) solubilizing collagen in a liquid solution, whereby surface area of the solubilized collagen molecules is exposed, to expose prions; and b) contacting the collagen in the liquid solution with sodium hydroxide, such that the concentration of sodium hydroxide in said liquid solution ranges from about 0.1M to about 0.35M, for a time period sufficient to inactivate said prions, at a temperature of about 25° C. or less, and wherein the collagen is capable of forming stable fibers after said inactivation.

18. The method of claim 17 wherein the collagen is atelopeptide collagen.

* * * * *